United States Patent
Kuwano et al.

(10) Patent No.: US 8,945,470 B2
(45) Date of Patent: Feb. 3, 2015

(54) SAMPLE ANALYZER AND SAMPLE ANALYZING METHOD

(75) Inventors: Keisuke Kuwano, Kobe (JP); Daigo Fukuma, Kobe (JP)

(73) Assignee: Sysmex Corporation, Kobe-Shi (JP)

( * ) Notice: Subject to any disclaimer, the term of this patent is extended or adjusted under 35 U.S.C. 154(b) by 649 days.

(21) Appl. No.: 12/751,284

(22) Filed: Mar. 31, 2010

(65) Prior Publication Data

US 2010/0248293 A1 Sep. 30, 2010

(30) Foreign Application Priority Data

Mar. 31, 2009 (JP) ................................. 2009-088109
Dec. 9, 2009 (JP) ................................. 2009-279819

(51) Int. Cl.
| | | |
|---|---|---|
| G01N 31/00 | (2006.01) |
| G01N 33/00 | (2006.01) |
| C12M 1/34 | (2006.01) |
| G01N 35/04 | (2006.01) |
| G01N 35/02 | (2006.01) |
| G01N 35/00 | (2006.01) |
| C12Q 1/02 | (2006.01) |
| C12M 3/00 | (2006.01) |
| G01N 35/10 | (2006.01) |

(52) U.S. Cl.
CPC ................ G01N 35/04 (2013.01); G01N 35/02 (2013.01); G01N 35/0092 (2013.01); G01N 35/026 (2013.01); G01N 35/00732 (2013.01); G01N 2035/00465 (2013.01); G01N 35/1081 (2013.01); G01N 2035/00326 (2013.01)
USPC ................... 422/65; 422/63; 422/64; 422/66; 422/67; 435/287.1; 435/287.3; 700/266; 436/43; 436/47; 436/50

(58) Field of Classification Search
USPC .............................................. 422/65; 436/47
See application file for complete search history.

(56) References Cited

U.S. PATENT DOCUMENTS

| 6,522,976 B2* | 2/2003 | Shiba et al. ..................... 702/22 |
| 6,723,288 B2* | 4/2004 | Devlin et al. ................... 422/65 |
| 7,101,715 B2* | 9/2006 | Devlin et al. ................... 436/43 |
| 2002/0106814 A1* | 8/2002 | Matsubara et al. ........... 436/180 |

(Continued)

FOREIGN PATENT DOCUMENTS

| JP | 63-217273 A | 9/1988 |
| JP | 2000-088860 A | 3/2000 |
| JP | 2003-066050 A | 3/2003 |

*Primary Examiner* — Bobby Ramdhanie
*Assistant Examiner* — Jennifer Wecker
(74) *Attorney, Agent, or Firm* — Sughrue Mion, PLLC

(57) ABSTRACT

The present invention is to present a sample analyzer comprising: a first measurement unit; a second measurement unit; a transport unit for transporting a sample container to the first measurement unit and the second measurement unit; and a controller configured to perform operations comprising: obtaining measurement item information indicating a measurement item of the sample contained in the sample container; and controlling the transport unit so as to transport the sample container to the second measurement unit when a first measurement item and a second measurement item different from the first measurement item are indicated in the measurement item information, and controlling the transport unit so as to transport the sample container to the first measurement unit or the second measurement unit when the first measurement item is indicated and the second measurement item is not indicated in the measurement item information.

6 Claims, 24 Drawing Sheets

(56) References Cited

U.S. PATENT DOCUMENTS

| | | | |
|---|---|---|---|
| 2003/0138355 A1* | 7/2003 | Tamura et al. | 422/63 |
| 2004/0053414 A1* | 3/2004 | Devlin, Sr. | 436/43 |
| 2004/0141882 A1* | 7/2004 | Mimura et al. | 422/63 |
| 2006/0247866 A1* | 11/2006 | Mishima et al. | 702/19 |
| 2009/0003981 A1* | 1/2009 | Miller | 414/267 |
| 2009/0068062 A1* | 3/2009 | Jafari et al. | 422/64 |
| 2009/0223308 A1* | 9/2009 | Fukuma | 73/863.01 |
| 2009/0227033 A1 | 9/2009 | Hamada et al. | |
| 2009/0325299 A1* | 12/2009 | Hamada et al. | 436/55 |

* cited by examiner

| HOLDING POSITION | MEASUREMENT ORDER | MEASUREMENT STATE | PRIORITY |
|---|---|---|---|
| 1 | CBC+DIFF | MEASURED | |
| 2 | CBC+DIFF | MEASURED | |
| 3 | CBC+DIFF | MEASURED | |
| 4 | CBC+DIFF,NRBC | WAITING FOR RETEST | 1 |
| 5 | CBC+DIFF | UNMEASURED | 2 |
| 6 | CBC+DIFF,RET | UNMEASURED | 3 |
| 7 | CBC+DIFF | UNMEASURED | 4 |
| 8 | CBC+DIFF | UNMEASURED | 5 |
| 9 | CBC+DIFF | UNMEASURED | 6 |
| 10 | CBC+DIFF | UNMEASURED | 7 |

FIG.18C

| HOLDING POSITION (F1) | MEASUREMENT ORDER (F2) | MEASUREMENT STATE (F3) | PRIORITY (F4) |
|---|---|---|---|
| 1 | CBC+DIFF | MEASURED | |
| 2 | | | |
| 3 | | | |
| 4 | | | |
| 5 | | | |
| 6 | | | |
| 7 | | | |
| 8 | | | |
| 9 | | | |
| 10 | | | |

FIG.18D

| HOLDING POSITION | MEASUREMENT ORDER | MEASUREMENT STATE | PRIORITY |
|---|---|---|---|
| 1 | CBC+DIFF | MEASURED | |
| 2 | CBC+DIFF,NRBC | UNMEASURED | 1 |
| 3 | | | |
| 4 | | | |
| 5 | | | |
| 6 | | | |
| 7 | | | |
| 8 | | | |
| 9 | | | |
| 10 | | | |

FIG.18F

| HOLDING POSITION (F1) | MEASUREMENT ORDER (F2) | MEASUREMENT STATE (F3 / PT) | PRIORITY (F4) |
|---|---|---|---|
| 1 | CBC+DIFF | MEASURED | |
| 2 | CBC+DIFF,NRBC | MEASURED | |
| 3 | CBC+DIFF | UNMEASURED | 1 |
| 4 | | | |
| 5 | | | |
| 6 | | | |
| 7 | | | |
| 8 | | | |
| 9 | | | |
| 10 | | | |

SAMPLE ANALYZER AND SAMPLE ANALYZING METHOD

FIELD OF THE INVENTION

The present invention relates to a sample analyzer which is provided with plural measurement units for measuring samples and a sample analyzing method of analyzing a sample by the sample analyzer.

BACKGROUND

Conventionally, there has been known an automatic analysis system for automatically transporting a plurality of samples and for analyzing the transported samples.

In Japanese Patent Publication No. S63-217273, there is disclosed an analysis system which includes: two analyzers of the same type; a start yard which sequentially delivers sample racks which has been set thereon; a conveyor which moves the sample rack delivered from the start yard; a sampler which receives the sample rack delivered by the conveyor and delivers sample containers held on the sample rack to a measuring section of the analyzer one by one; a stock yard which collects sample racks holding sample containers containing samples which have been measured; and a controller which controls operations of the respective components described above. In the analysis system, the sample racks are sequentially sent to an analyzer which is empty, so that the entire processing speed is increased.

In the analysis system disclosed, in Japanese Patent Publication No. S63-217273, however, both of the two analyzers should allow a measurement of a sample on all measurement items likely to be necessary for a measurement.

SUMMARY

The scope of the present invention is defined solely by the appended claims, and is not affected to any degree by the statements within this summary.

A first aspect of the present invention is a sample analyzer comprising: a first measurement unit for measuring a sample; a second measurement unit for measuring a sample; a transport unit for transporting a sample container containing a sample to the first measurement unit and the second measurement unit; and a controller configured to perform operations comprising: obtaining measurement item information indicating a measurement item of the sample contained in the sample container; and controlling the transport unit so as to transport the sample container to the second measurement unit when a first measurement item and a second measurement item different from the first measurement item are indicated in the measurement item information, and controlling the transport unit so as to transport the sample container to the first measurement unit or the second measurement unit when the first measurement item is indicated and the second measurement item is not indicated in the measurement item information.

A second aspect of the present invention is a sample analyzer comprising: a transport unit for transporting a plurality of sample containers, each containing a sample; a first measurement unit for aspirating a sample from a sample container transported by the transport unit, and measuring the aspirated sample; a second measurement unit for aspirating a sample from a sample container transported by the transport unit, and measuring the aspirated sample; and a controller configured to perform operations comprising: obtaining measurement item information indicating measurement items of samples contained in the plurality of sample containers; and controlling the transport unit so as to transport a second sample container to the second measurement unit ahead of a first sample container, the first sample container containing a first sample whose measurement item information indicates a first measurement item and does not indicate a second measurement item different from the first measurement item, the second sample container containing a second sample whose measurement item information indicates the first and the second measurement items, when the first measurement unit is not ready to aspirate a sample and the second measurement unit is ready to aspirate a sample.

A third aspect of the present invention is a sample analyzing method comprising the steps of: (a) transporting a sample container, which contains a sample to be measured, to a second measurement unit which measures the sample on a first measurement item and a second measurement item different from the first measurement item, and measuring the sample by the second measurement unit, when the sample is to be measured on the first and the second measurement items; and (b) transporting the sample container to a first measurement unit which measures the sample on the first measurement item and does not measure the sample on the second measurement item, or to the second measurement unit, and measuring the sample by the first measurement unit or the second measurement unit to which the sample container has been transported, when the sample is to be measured on the first measurement item and not to be measured on the second measurement item.

BRIEF DESCRIPTION OF THE DRAWINGS

FIG. 18C is a diagram schematically illustrating an example of a state of the sample processing table;

FIG. 18D is a diagram schematically illustrating an example of a state of the sample processing table;

FIG. 18F is a diagram schematically illustrating an example of a state of the sample processing table;

DETAILED DESCRIPTION OF THE EMBODIMENT

Hereinafter, an exemplary embodiment of the present invention will be described with reference to the drawings.

In this embodiment, there is provided a sample analyzer which includes a first measurement unit which is allowed to measure a sample regarding a first measurement item and is not allowed to measure a sample regarding a second measurement item different from the first measurement item, a second measurement unit which is allowed to measure a sample regarding both the first measurement item and the second measurement item, and a transport unit which transports a sample to the first measurement unit and the second measurement unit. The transport unit transports a sample to be subjected to measurement on both the first measurement item and the second measurement item to the second measurement unit, and transports a sample to be subjected to measurement on only the first measurement item to any one of the first measurement unit and the second measurement unit according to the operation states of the first measurement unit and the second measurement unit. Further, the first measurement item indicates a measurement item which can be measured by plural measurement units. In addition, the second measurement item indicates a measurement item which can be measured by a predetermined measurement unit among the plural measurement units but not the other measurement unit.

[Configuration of Sample Analyzer]

Figure 1A:
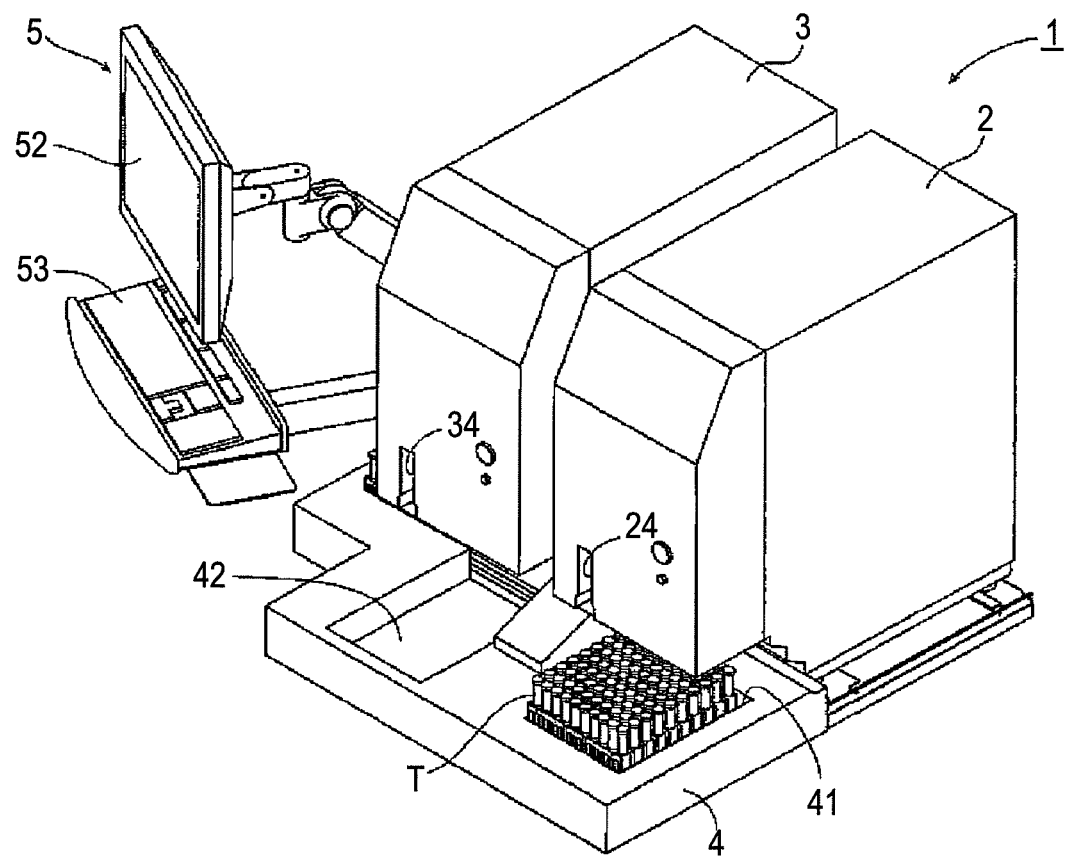
FIG. 1A is a perspective view illustrating the entire configuration of a sample analyzer according to Embodiment 1.
Figure 1B:
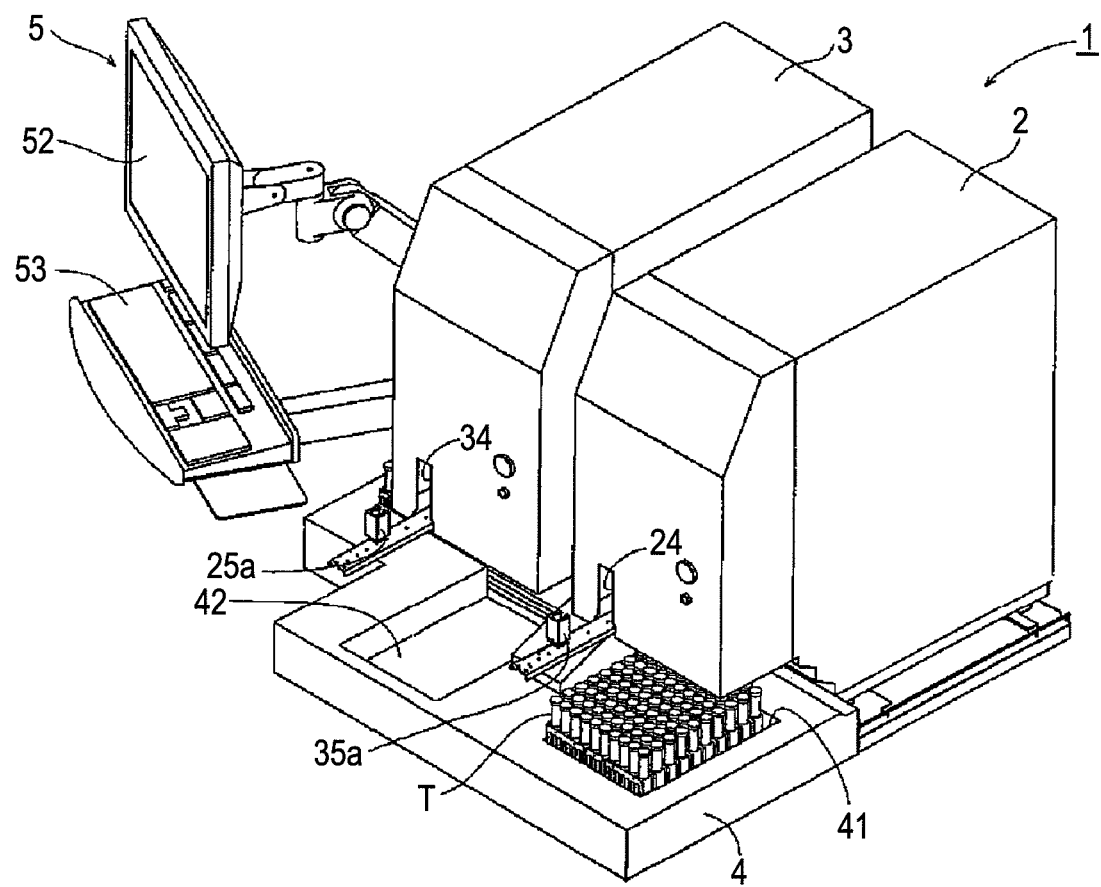
FIG. 1B is a perspective view illustrating the entire configuration of a sample analyzer according to Embodiment 1.

FIGS. 1A and 1B are perspective views each illustrating the entire configuration of the sample analyzer according to this embodiment. The sample analyzer 1 according to this embodiment is a multiple blood cell analyzing apparatus which detects the white blood cells, the red blood cells, the platelets and the like which are included in the blood sample, and counts each blood cell. As shown in FIGS. 1A and 1B, the sample analyzer 1 is provided with a first measurement unit 2, a second measurement unit 3, a sample transport unit 4 which is disposed on a front side surface of the first measurement unit 2 and the second measurement unit 3, and an information processing unit 5 which can control the first measurement unit 2, the second measurement unit 3 and the sample transport unit 4.

Figure 2:
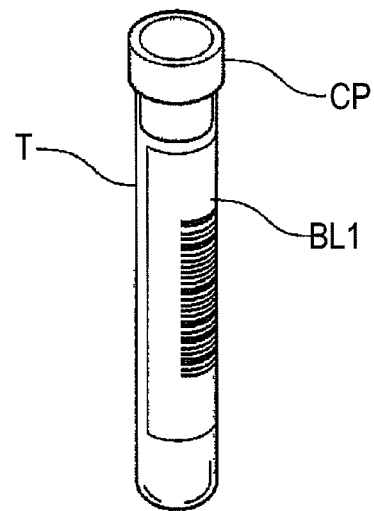
FIG. 2 is a perspective view illustrating an appearance of a sample container.
Figure 3:
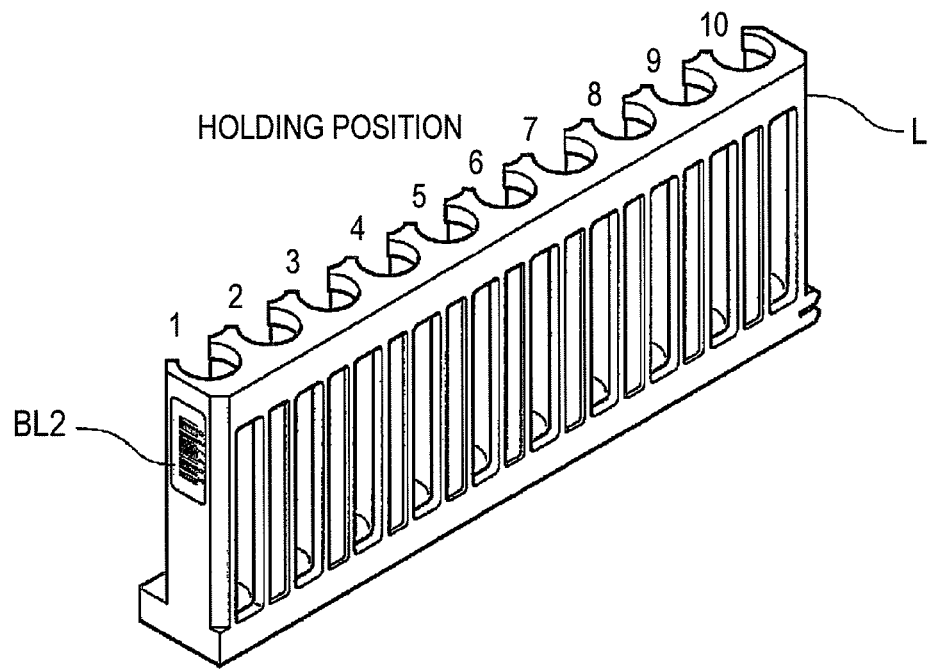
FIG. 3 is a perspective view illustrating an appearance of a sample rack.

FIG. 2 is a perspective view illustrating an appearance of the sample container which contains a sample, and FIG. 3 is a perspective view illustrating an appearance of a sample rack which holds plural sample containers. As shown in FIG. 2, the sample container T is formed in a tubular shape, and the upper end is opened. A blood sample gathered from a patient is contained in the sample container, and the opening on the upper end is sealed by a cap section CP. The sample container T is made of a transparent glass or a transparent synthetic resin, so that the blood sample therein is visible. In addition, the side surface of the sample container T is patched with the bar-code label BL1. A bar-code indicating the sample ID is printed on the bar-code label BL1. Returning to FIG. 3, the sample rack L can arrange and hold 10 sample containers T. Each sample container T is held on in a vertical state (upright state) to the sample rack L. In addition, a bar-code label BL2 is patched on the side surface of the sample rack L. A bar-code indicating the rack ID is printed on the bar-code label BL2.

<Configuration of Measurement unit>

Figure 4:
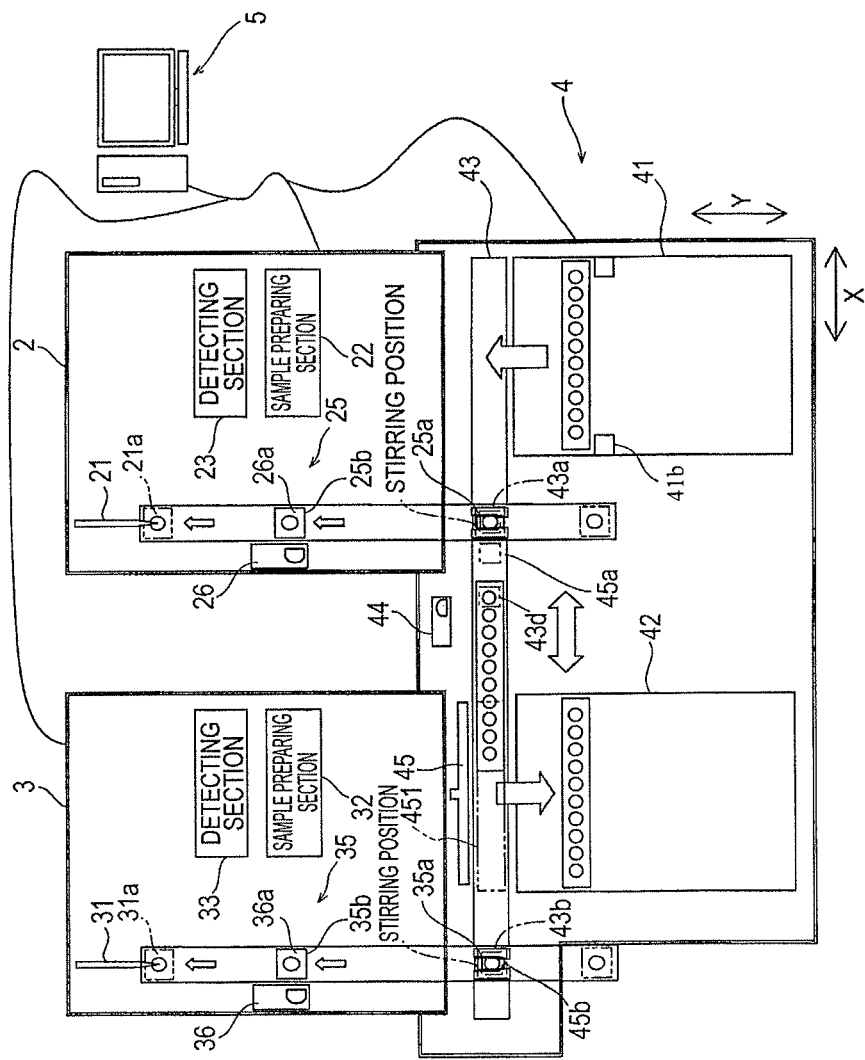
FIG. 4 is a block diagram illustrating the configuration of a measurement unit according to Embodiment 1.

The first measurement unit 2 is disposed on the upstream side in a transport direction (X direction shown in FIG. 4) of the sample of the sample transport unit 4. The second measurement unit 3 is disposed on the downstream side in the transport direction. FIG. 4 is a block diagram illustrating the configuration of the measurement unit. As shown in FIG. 4, the first measurement unit 2 includes a sample aspirating section 21 which aspirates blood as the sample from the sample container (blood collection tube) T, a sample preparing section 22 which prepares a measuring reagent to be used in measuring of blood components, such as a blood cell, from the blood aspirated by the sample aspirating section 21, and a detecting section 23 which detects (measures) the blood cell from the measuring reagent prepared by the sample preparing section 22. In addition, the first measurement unit 2 further includes a loading port 24 (see FIGS. 1A and 1B) which is used to load the sample container T accommodated in the sample rack L, which is transported by the rack transport section 43 of the sample transport unit 4, into the first measurement unit 2, and a sample container transport section 25 which loads the sample container T from the sample rack L into the first measurement unit 2 and transports the sample container T up to an aspirating position by the sample aspirating section 21.

As shown in FIG. 4, an aspiration tube (not shown) is provided at the tip end of the sample aspirating section 21. In addition, the sample aspirating section 21 is configured to be vertically moved, and moved downward, so that the aspiration tube penetrates into the cap section CP of the sample container T transported to the aspiration position so as to aspirate the blood in the sample container.

The sample preparing section 22 is provided with plural reaction chambers (not shown). In addition, the sample preparing section 22 is connected to the reagent container (not shown), and can supply a reagent, such as a staining reagent, a hemolytic agent, or a diluting fluid, to the reaction chamber. The sample preparing section 22 is also connected to the aspiration tube of the sample aspirating section 21, and can supply the blood sample aspirated by the aspiration tube to the reaction chamber. The sample preparing section 22 mixes and stirs the sample in the reaction chamber with the reagent, and prepares the sample (measuring reagent) for measuring by the detecting section 23.

The detecting section 23 can detect the red blood cells (RBC) and the platelets (PLT) by using a sheath flow DC detection method. In detecting RBCs and PLTs by using the sheath flow DC detection method, a measuring reagent in which a sample and a diluting fluid are mixed is measured, and measurement data obtained in this manner is analyzed and processed by the information processing unit 5 so as to obtain numerical data of the RBCs and PLTs. In addition, the detecting section 23 is configured to detect hemoglobin (HGB) by using a SLS-hemoglobin method and detect white blood cells (WBC), neutrophils (NEUT), lymphocytes (LYMPH), eosinophils (EO), basophil (BASO) and monocytes (MONO) by using a flow cytometry method using semiconductor lasers. The detecting section 23 performs WBC detection not accompanying detection of five classifications of the white blood cells, the detection of NEUT, LYMPH, EO, BASO, and MONO, and WBC detection along with performing detection of the five classifications of the white blood cells in different detection methods. In the WBC detection not accompanying detection of the five classifications of the white blood cells, the measuring reagent in which the sample, the hemolytic agent, and the diluting fluid are mixed is measured, and measurement data obtained in this manner is analyzed and processed by the information processing unit 5 so as to obtain numerical data of the WBC. On the other hand, in the WBC detection accompanying the five classifications of the white blood cell, the measuring reagent in which the reagent, the hemolytic agent, and the diluting fluid for the five classifications of the white blood cells are mixed is measured, the measurement data obtained in this manner is analyzed and processed by the information processing unit 5 so as to obtain numerical data of the NEUT, LYMPH, EO, BASO, MONO, and WBC.

The above-mentioned WBC, RBC, PLT, and HGB include a measurement item referred to as a CBC item. The WBC, RBC, PLT, HGB, NEUT, LYMPH, EO, BASO, and MONO include a measurement item referred to as a CBC+DIFF item. In this embodiment, the CBC+DIFF item is a measurement item which can be commonly measured in the first measurement unit 2 and the second measurement unit 3, and is the first measurement item which is measured on all the samples. For this reason, a reagent for measuring the CBC+DIFF item is mounted on both the first measurement unit 2 and the second measurement unit 3.

Figure 5:
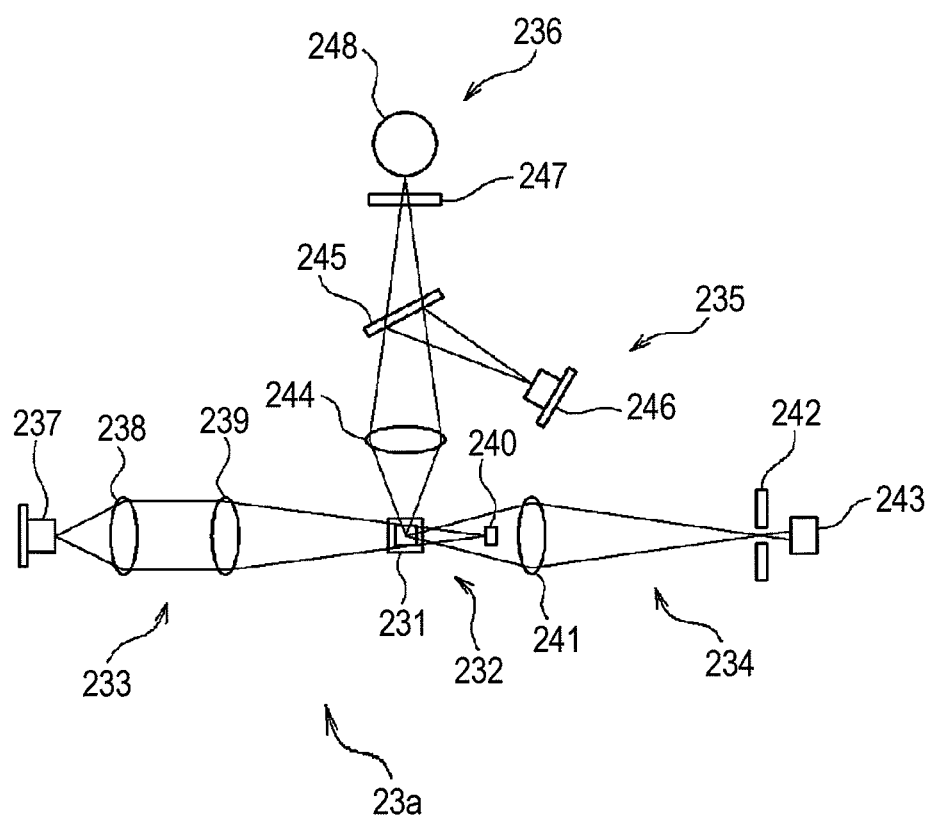
FIG. 5 is a schematic view illustrating an outline configuration of an optical detecting section for detecting the WBC/DIFF (five classifications of the white blood cells)

FIG. 5 shows the outline configuration of an optical detecting section for detecting WBC/DIFF (five classifications of the white blood cells) which is provided in the detecting section 23. The optical detecting section 23a is configured to send the measuring reagent into a flow cell 231, generate a liquid current in the flow cell 231, and perform measuring by irradiating the blood cell included in the liquid current passing through the flow cell 231 with a semiconductor laser light. The optical detecting section includes a sheath flow system 232, a beam spot forming system 233, a forward-scattered light receiving system 234, a side-scattered light receiving system 235, and a side-fluorescence light receiving system 236.

The sheath flow system 232 is configured such that the sample flows in the flow cell 231 in a state of being surrounded by a sheath fluid and in a state where the blood cells are aligned in a single line, so that the accuracy and reproducibility of the blood cell counting can be improved. The beam spot forming system 233 is configured such that light irradiated from a semiconductor laser 237 passes through a collimator lens 238 and a condenser lens 239 so as to irradiate the flow cell 231. In addition, the beam spot forming system 233 is provided with a beam stopper 240.

The forward-scattered light receiving system 234 is configured such that the forward-scattered light is condensed by a forward-condensing lens 241, and the light passing through a pin hole 242 is received by a photo diode (forward-scattered light receiving section) 243.

The side-scattered light receiving system 235 is configured such that the side-scattered light is condensed by a side-condensing lens 244, and a part of the light is reflected on a dichroic mirror 245 so as to be received by a photo diode (side-scattered light receiving section) 246.

Light scattering is a phenomenon occurring such that the particles of the blood cells act as an obstacle to light in the advancing direction thereof, and the light is changed in the advancing direction. By detecting the scattered light, information on the size or the material of the particle can be obtained. In particular, the information on the size of the particle (blood cell) can be obtained from the forward-scattered light. In addition, the information on the content of the particle can be obtained from the side-scattered light. When a laser light is irradiated to the blood cell particle, the side-scattered light intensity depends on the complexity of the inside of the cell (shape, size, density, or granulated amount of nucleus). Therefore, using the characteristics of the side-scattered light intensity, the measurement of the white blood cell classification and the other measurements can be carried out.

The side-fluorescence light receiving system 236 is configured such that the light that passed through the dichroic mirror 245 further passes through a spectral filter 247 and is received by an avalanche photodiode (fluorescence light receiving system) 248.

When light is irradiated to a fluorescent material such as a stained blood cell, light is generated of which the wavelength is longer than that of the irradiated light. If staining is sufficiently performed, the fluorescence intensity becomes stronger. By measuring the fluorescence intensity, the information on the staining degree of the blood cell can be obtained. Therefore, by a difference of the (side) fluorescence intensity, the measurement of the white blood cell classification and the other measurement can be carried out.

Returning to FIG. 4, the configuration of the sample container transport section 25 will be described. The sample container transport section 25 is provided with a hand section 25a which can grasp the sample container T. The hand section 25a is provided with a pair of grasping members which are disposed so as to face each other. The grasping members can be close to or away from each other. The grasping members can grasp the sample container T by being close to each other in a state where the sample container T is interposed therebetween. In addition, the sample container transport section 25 can move the hand section 25a in a vertical direction and in a backward or forward direction (Y direction), and can also oscillate the hand section 25a. Thereafter, the sample container T which is contained in the sample rack L and positioned at the first sample supply position 43a is grasped by the hand section 25a. In this state, the hand section 25a moves upward, so that the sample container T is pulled out of the sample rack L, and the hand section 25a is oscillated, so that the sample in the sample container T can be stirred.

In addition, the sample container transport section 25 is provided with a sample container setting section 25b which includes a hole section through which the sample container T can be inserted. The sample container T grasped by the above-mentioned hand section 25a moves after the stirring is completed. Then, the grasped sample container T is inserted into the sample container setting section 25b. Thereafter, the grasping members are away from each other, so that the sample container T is released from the hand section 25a, and the sample container T is set in the sample container setting section 25b. The sample container setting section 25b can horizontally move in the Y direction by a driving force of the stepping motor (not shown).

In the first measurement unit 2, a bar-code reading section 26 is provided. The sample container setting section 25b can move to a bar-code reading position 26a near the bar-code reading section 26 and a aspirating position 21a carried out by the sample aspirating section 21. When the sample container setting section 25b moves to the bar-code reading position 26a, the set sample container T is horizontally rotated by a rotation mechanism (not shown) and the sample bar-code is read by the bar-code reading section 26. Accordingly, even when the bar-code label BL1 of the sample container T is positioned on the opposite side with respect to the bar-code reading section 26, the bar-code label BL1 can face the bar-code reading section 26 by rotating the sample container T and the bar-code reading section 26 can read the sample bar-code. In addition, when the sample container setting section 25b is moved to the aspiration position, the sample is aspirated from the set sample container T by the sample aspirating section 21.

Next, the configuration of the second measurement unit 3 will be described. The configuration of the second measurement unit 3 is the same as that of the first measurement unit 2. The second measurement unit 3 includes a sample aspirating section 31, a sample preparing section 32 which prepares a measuring reagent to be used in measuring of the blood components, such as a blood cell, from the blood aspirated by the sample aspirating section 31, and a detecting section 33 which detects the blood cell from the measuring reagent prepared by the sample preparing section 32. In addition, the second measurement unit 3 further includes a loading port 34 (see FIGS. 1A and 1B) which is used to load the sample container T accommodated in the sample rack L, which is transported by the rack transport section 43 of the sample transport unit 4, into the second measurement unit 3, and a sample container transport section 35 which loads the sample container T from the sample rack L into the second measurement unit 3 and transports the sample container T up to an aspirating position by the sample aspirating section 31. The sample aspirating section 31, the sample preparing section 32, the detecting section 33, the loading port 34, the sample container transport section 35, and the bar-code reading section 36 are configured of the same hardware as those of the sample aspirating section 21, the sample preparing section 22, the detecting section 23, the loading port 24, and the sample container transport section 25, so that the descriptions thereof will be omitted.

In the second measurement unit 3, a reagent for measuring a reticulocyte (RET) and a nucleated red blood cell (NRBC) in addition to a reagent for measuring each measurement item regarding. WBC, RBC, PLT, HGB, NEUT, LYMPH, EO, BASO, and MONO which are the above-mentioned CBC+DIFF item and can be measured by the first measurement unit 2. In addition, the measurement operation of the first measurement unit 2 is controlled by a thread corresponding to the CBC+DIFF item which is included in a process operated by executing a computer program 54a to be described later. On the other hand, the measurement operation of the second measurement unit 3 is controlled by a thread corresponding to the measurement of the measurement item of the RET and NRBC in addition to the thread corresponding to the measurement of the above-mentioned CBC+DIFF item. Therefore, in addition to the CBC+DIFF item which can be measured by the first measurement unit 2, the second measurement unit 3 can measure a sample regarding the measurement item of the RET and NRBC. The RET and NRBC become a second measurement item which is measured only regarding some samples. In the second measurement unit 3, the RET measurement is carried out such that a measuring reagent is prepared by mixing a reagent for measuring the RET with a sample and the measuring reagent is supplied to an optical detecting section for detecting the WBC/DIFF (five classifications of the white blood cells) of the detecting section 33. In addition, the NRBC measurement is carried out such that a measuring reagent is prepared by mixing a reagent for measuring the NRBC with a sample and the measuring reagent is supplied to an optical detecting section for detecting the WBC/DIFF (five classifications of the white blood cells) of the detecting section 33.

The first measurement unit 2 and the second measurement unit 3 as described above perform cleaning of the sample aspirating sections 21 and 31 while a measuring reagent prepared from one sample is measured by the detecting sections 23 and 33. In addition, the sample container T of another sample can be loaded to the inside thereof so as to aspirate the sample by the sample aspirating sections 21 and 31.

<Configuration of Sample Transport Unit>

Next, the configuration of the sample transport unit 4 will be described. As shown in FIGS. 1A and 1B, the sample transport unit 4 is disposed in front of the first measurement unit 2 and the second measurement unit 3 of the sample analyzer 1. The sample transport unit 4 can transport the sample rack L in order to supply the sample to the first measurement unit 2 and the second measurement unit 3.

Figure 6:
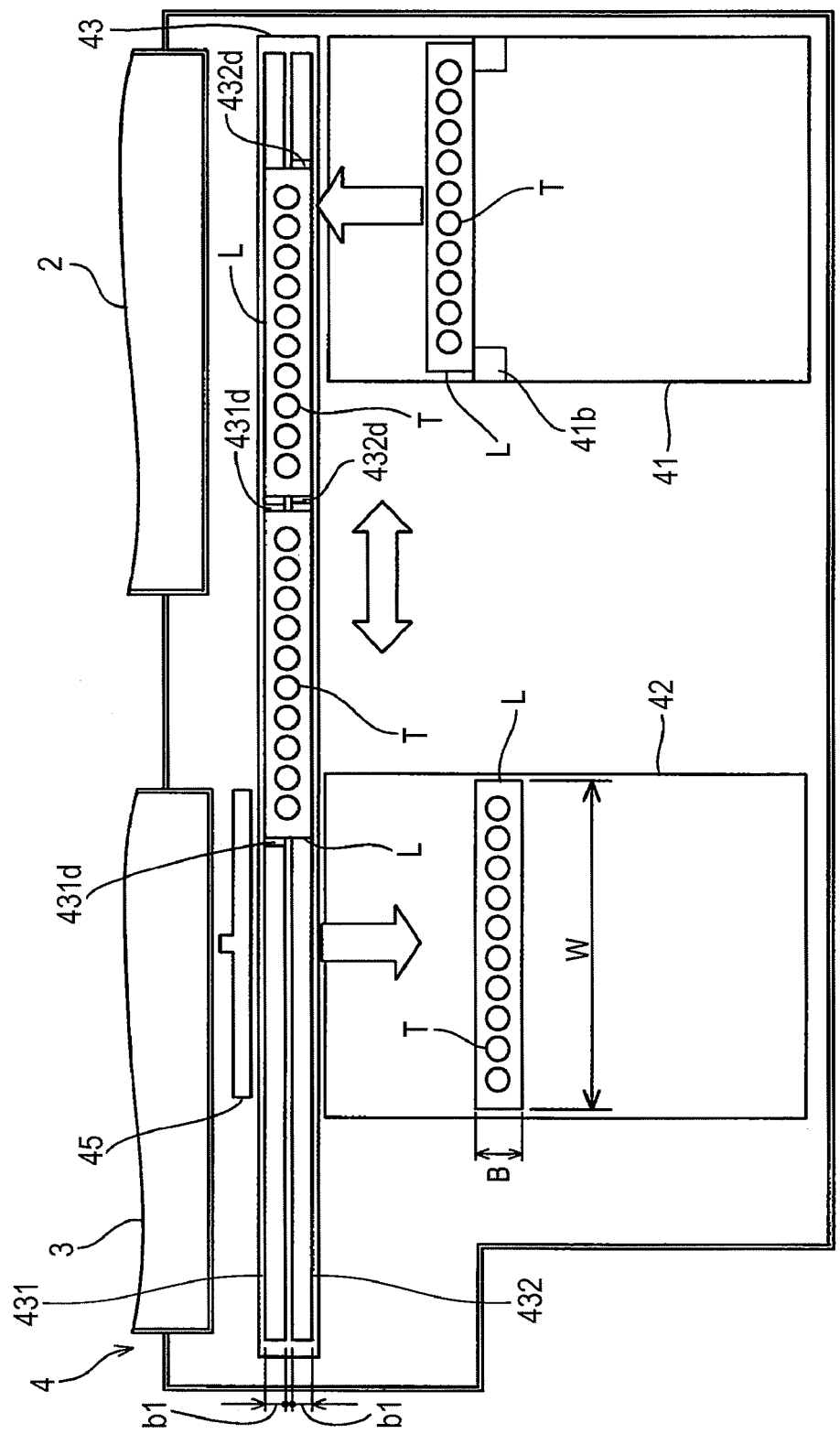
FIG. 6 is a plan view illustrating the configuration of a sample transport unit.

FIG. 6 is a plan view illustrating the configuration of the sample transport unit 4. As shown in FIG. 6, the sample transport unit 4 is provided with: a before-analysis rack holding section 41 which can temporarily hold the plural sample racks L each holding a sample container T which accommodates samples before analysis is carried out thereon; an after-analysis rack holding section 42 which can temporarily hold the plural sample racks L each holding a sample container T in which the sample is aspirated by the first measurement unit 2 or the second measurement unit 3; the rack transport section 43 which horizontally moves the sample rack L in a straight line in the direction of arrow X in the drawing in order to supply the sample to the first measurement unit 2 or the second measurement unit 3 and transports the sample rack L received from the before-analysis rack holding section 41 to the after-analysis rack holding section 42; a bar-code reading section 44 (see FIG. 4); and sample container sensors 45a and 45b (see FIG. 4) each detecting the existence of the sample container T.

The before-analysis rack holding section 41 has a quadrangular shape in plane view, and the width thereof is slightly larger than the width of the sample rack L. The before-analysis rack holding section 41 is formed to be lower by one stage than the surrounding surface, and on an upper face thereof, the before-analysis sample racks L are mounted. In addition, the rack sending sections 41b are provided in both faces of the before-analysis rack holding section 41 so as to be protruded inward. The rack sending sections 41b protrude so as to engage with the sample rack L. In this state, the rack sending sections are moved backward (a direction so as to be closer to the rack transport section 43) and thus the sample rack L is moved backward. The rack sending sections 41b are configured to be driven by a stepping motor (not shown) which is provided below the before-analysis rack holding section 41.

As shown in FIG. 6, the rack transport section 43 can move the sample rack L sent by the before-analysis rack holding section 41 in the X direction as described above. On the transport path of the sample rack L by the rack transport section 43, there are a first sample supply position 43a for supplying a sample to the first measurement unit 2 and a second sample supply position 43b for supplying a sample to the second measurement unit 3 which are shown in FIG. 4. Returning to FIG. 4, when the sample transport unit 4 is controlled by the information processing unit 5 so as to transport the sample to the first sample supply position 43a or the second sample supply position 43b, the hand section 25a or 35a of the corresponding measurement unit grasps the sample container T and takes out the sample container T from the sample rack L so as to supply the sample to the first measurement unit 2 or the second measurement unit 3. As a result, the hand section 25a or 35a grasping the sample container T enters into the housing of the first measurement unit 2 or the second measurement unit 3 as described above, and thereby the sample is loaded into the first measurement unit 2 or the second measurement unit 3. The rack transport section 43 can also transport the sample rack L while the sample is being loaded in the first measurement unit 2 or the second measurement unit 3. Therefore, since another sample cannot be loaded into the measurement unit while one of the first measurement unit 2 and the second measurement unit 3 is being loaded with the sample, the sample rack L can be transported to the other measurement unit so as to load the sample.

Figure 7:
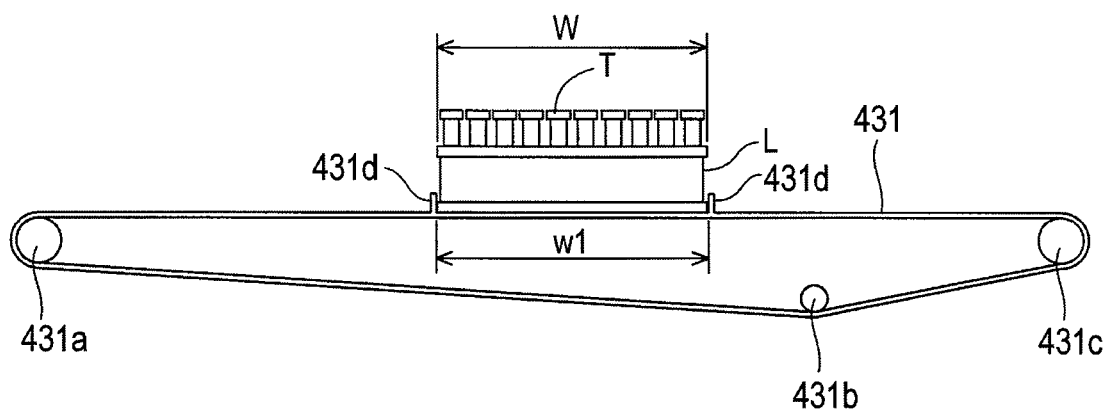
FIG. 7 is a front view illustrating the configuration of a first belt of a sample transport unit.
Figure 8:
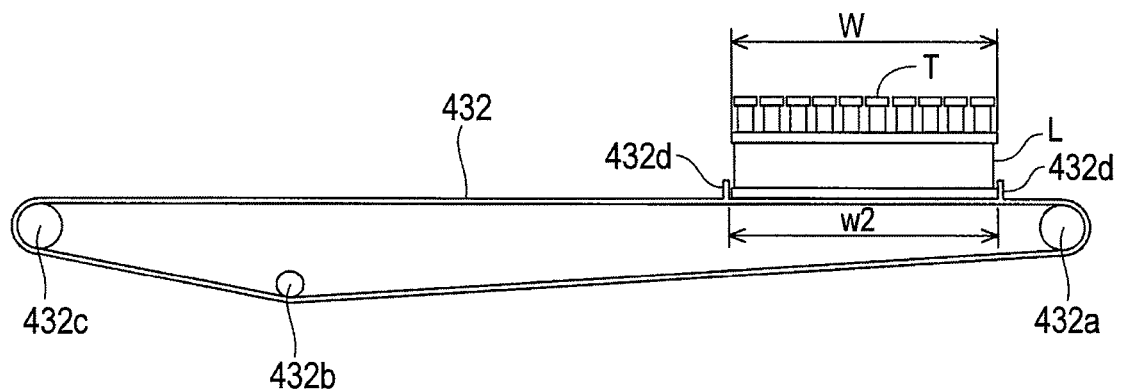
FIG. 8 is a front view illustrating the configuration of a second belt of a sample transport unit.

Here, the configuration of the rack transport section 43 will be described with reference to FIGS. 6 to 8. As shown in FIG. 6, the rack transport section 43 has two independently operable belts, that is, a first belt 431 and a second belt 432. Width b1 in a direction of the arrow Y of the first belt 431 and the second belt 432 is equal to or less than half of a width B in the direction of the arrow Y of the sample rack L. The first belt 431 and the second belt 432 are disposed in parallel so as not to protrude from the width B of the sample rack L when the rack transport section 43 transports the sample rack L. FIG. 7 is a front view illustrating the configuration of the first belt 431, and FIG. 8 is a front view illustrating the configuration of the second belt 432. As shown in FIGS. 7 and 8, the first belt 431 and the second belt 432 are annularly formed. The first belt 431 is disposed so as to surround rollers 431a to 431c and the second belt 432 is disposed so as to surround rollers 432a to 432c. In the outer peripheral section of the first belt 431, two protrusions 431d are provided so as to have an inner width w1 slightly larger (for example, 1 mm) than a width W in the X direction of the sample rack L. Similarly, as shown in FIG. 8, in the outer peripheral section of the second belt 432, two protrusions 432d are provided so as to have the same inner width w2 as the inner width w1. The first belt 431 is configured such that the sample rack L held inside of the two protrusions 431d is moved in the direction of the arrow X by being moved along the outer peripheries of the rollers 431a to 431c by a stepping motor (not shown). The second belt 432 is configured such that the sample rack L held inside of the two protrusions 432d is moved in the direction of the arrow X by being moved along the outer peripheries of the rollers 432a to 432c by a stepping motor (not shown). In addition, the first belt 431 and the second belt 432 are configured so as to move the sample rack L independently of each other. Therefore, the rack transport section 43 can transport the sample rack L such that the sample is transported up to the first sample supply position 43a, the second sample supply position 43b, and the reading position 43d for reading the bar-code printed on the bar-code label BL1 of the sample container T by the bar-code reading section 44.

Returning to FIG. 4, the bar-code reading section 44 is configured to read the bar-code printed on the bar-code label BL1 of the sample container T shown in FIG. 2, and to read the bar-code printed on the bar-code label BL2 which is attached to the sample rack L. In addition, the bar-code reading section 44 is configured to read the bar-code of the sample container T while the sample container T of the subject accommodated in the sample rack L is being rotated by a rotation apparatus (not shown). Therefore, even when the bar-code of the sample container T is attached to an opposite side with respect to the bar-code reading section 44, the bar-code can face the bar-code reading section 44 by rotating the sample container T. In addition, the bar-code printed on the bar-code label BL2 of the sample rack L is uniquely assigned to each rack and used to manage the analysis result of the sample.

Each of the sample container sensors 45a and 45b is a contact sensor and has a contact piece, a light-emitting element for emitting light, and a light-receiving element (not shown). Each of the sample container sensors 45a and 45b is configured such that the contact piece is bent when brought into contact with a substance to be detected which is a detection object and the light emitted from the light-emitting element is thus reflected by the contact piece and enters the light-receiving element. Accordingly, while the sample container T which is a detection object accommodated in the sample rack L passes under the sample container sensors 45a and 45b, the contact piece is bent by the sample container T and the sample container T can be detected. The sample container sensor 45a is provided on the first sample supply position 43a, and the sample container sensor 45b is provided on the second sample supply position 43b. Therefore, the existence of the sample container T at the first sample supply position 43a can be detected by the sample container sensor 45a, and the existence of the sample container T at the second sample supply position 43b can be detected by the sample container sensor 45b.

At the downstream end of the rack transport section 43 in the transport direction, an after-analysis rack holding section 42 to be described is provided. A rack delivery section 45 is provided in the rear side of the after-analysis rack holding section 42. The rack delivery section 45 is configured to horizontally move in a straight line in the direction of the arrow Y by a driving force of the stepping motor (not shown). Therefore, when the sample rack L is transported to a position 451 (hereinafter, referred to as "after-analysis rack delivery position") between the after-analysis rack holding section 42 and the rack delivery section 45, the sample rack L can be pushed and moved into the after-analysis rack holding section 42 by moving the rack delivery section 45 toward the after-analysis rack holding section 42.

The after-analysis rack holding section 42 has a quadrangular shape in plane view, and the width thereof is slightly larger than the width of the sample rack L. The after-analysis rack holding section 42 is formed to be lower by one stage than the surrounding surface, and on an upper face thereof, the analyzed sample racks L are held. The after-analysis rack holding section 42 is connected to the above-mentioned rack transport section 43 and, as described above, sends the sample rack L from the rack transport section 43 by the rack delivery section 45.

According to the configuration as described above, the sample transport unit 4 moves the sample rack L mounted on the before-analysis rack holding section 41 to the rack transport section 43, and is further transported by the rack transport section 43 so that the sample can be supplied to the first measurement unit 2 or the second measurement unit 3. In addition, the sample rack L accommodating the samples which are completely aspirated is moved to the after-analysis rack delivery position (not shown) by the rack delivery section 43, and delivered to the after-analysis rack holding section 42 by the rack delivery section 45. When the plural sample racks L are mounted on the before-analysis rack holding section 41, the sample racks L accommodating the samples which are completely analyzed are sequentially delivered to the after-analysis rack holding section 42 by the rack delivery section 45. The plural sample racks L are stored in the after-analysis rack holding section 42.

<Configuration of Information Processing Unit>

Figure 9:
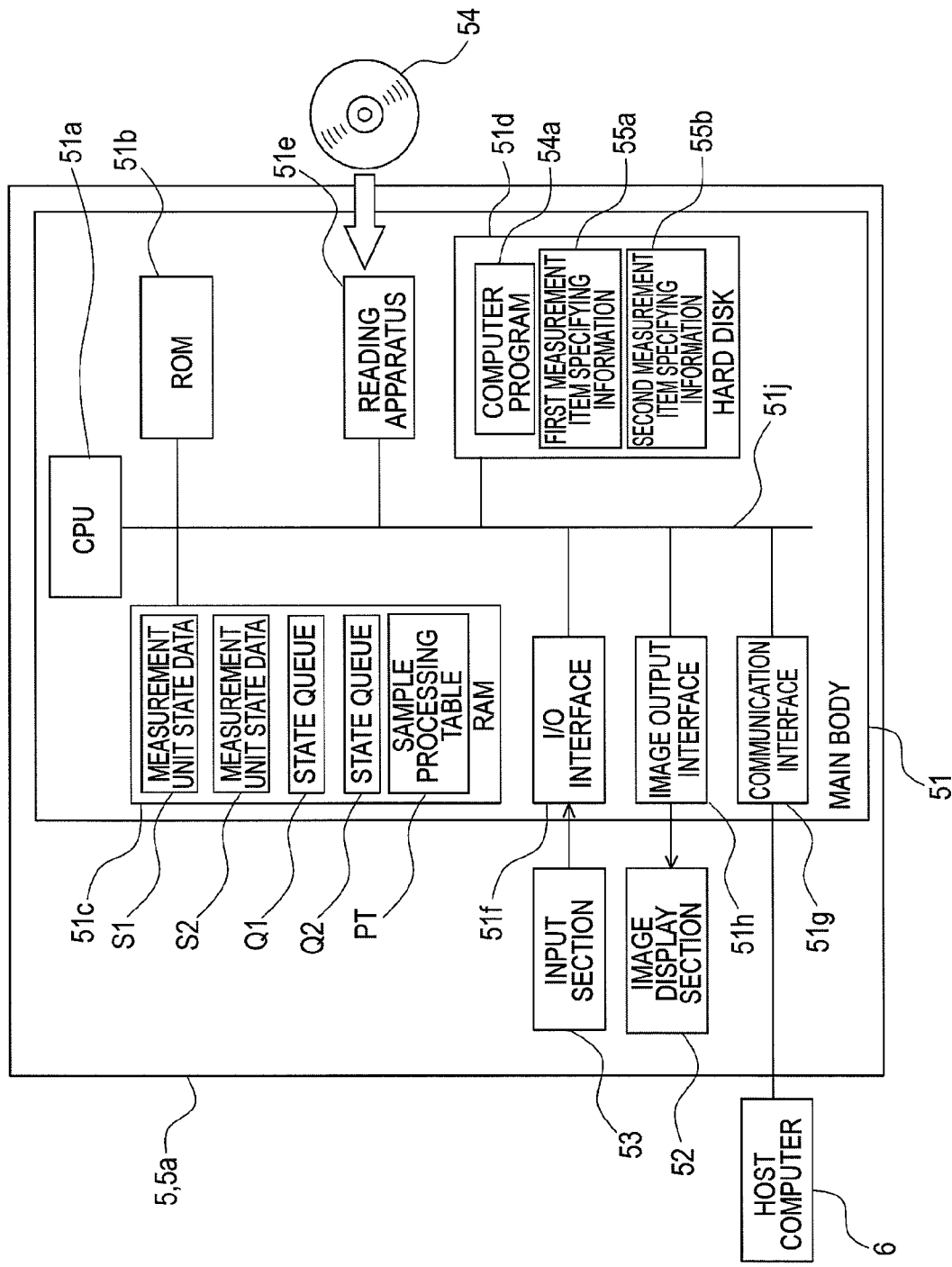
FIG. 9 is a block diagram illustrating the configuration of an information processing unit according to an embodiment.

Next, the configuration of the information processing unit 5 will be described. The information processing unit 5 is composed of a computer. FIG. 9 is a block diagram illustrating the configuration of the information processing unit 5. The information processing unit 5 is realized by a computer 5a. As shown in FIG. 9, the computer 5a includes a main body 51, an image display section 52 and an input section 53. The main body 51 includes a CPU 51a, a ROM 51b, a RAM 51c, a hard disk 51d, a reading device 51e, an I/O interface 51f, a communication interface 51g and an image output interface 51h. The CPU 51a, ROM 51b, RAM 51c, hard disk 51d, reading device 51e, I/O interface 51f, communication interface 51g and image output interface 51h are connected to each other by a bus 51j.

The CPU 51a can execute a computer program loaded to the RAM 51c. The CPU 51a executes a computer program 54a for analyzing a sample and for controlling the first measurement unit 2, the second measurement unit 3 and the sample transport unit 4, which will be described later, so that the computer 5a functions as the information processing unit 5.

The ROM 51b is composed of a mask ROM, a PROM, an EPROM, an EEPROM or the like and the computer program executed by the CPU 51a and data used for the computer program are recorded in the ROM.

The RAM 51c is composed of a SRAM, a DRAM or the like. The RAM 51c is used to read the computer program 54a recorded in the hard disk 51d. In addition, the RAM is used as an operating area of the CPU 51a when the CPU 51a executes a computer program.

In the RAM 51c, measurement unit state data areas S1 and S2 representing the states of the first measurement unit 2 and the second measurement unit 3 are provided. In the measurement unit state data areas S1 and S2, any one data of "Sample Loading Possible" and "Sample Loading Impossible" is stored. Here, when the measurement unit does not carry out the measurement operation such as a loading operation of the sample container, a preparing operation of the measuring reagent and a detecting operation of the blood cell in the measuring reagent but in a standby state where the measurement unit stands by to be loaded with the sample container, the state of the measurement unit becomes the state of "Sample Loading Possible". In addition, when the measurement unit carries out the loading operation of the sample container, the aspirating operation of the sample from the sample container and the unloading operation of the sample container from the measurement unit, the state of the measurement unit becomes the state of "Sample Loading Impossible". Furthermore, when the measurement unit carries out the preparing operation of the measuring reagent, the detecting operation of the blood cell in the measuring reagent by the detecting sections 23 and 33 and the cleaning operation, the state of the measurement unit becomes the state of "Sample Loading Possible" in which a new sample can be loaded.

In addition, in the RAM 51c, areas of state queues Q1 and Q2 in which the state data of the first measurement unit 2 and the second measurement unit 3 is stored are provided. The state queues Q1 and Q2 receive the state data of the first measurement unit 2 and the second measurement unit 3 in real time, and store the state data in a FIFO (first-in first-out) list structure.

In the hard disk 51d, various computer programs for execution by the CPU 51a, such as an operating system and an application program, and data which is used to execute the computer programs, are installed. The computer program 54a to be described later is also installed in the hard disk 51d.

In addition, in the hard disk 51d, first measurement item specifying information 55a for specifying a measurement item which can be measured by the first measurement unit 2, and second measurement item specifying information 55b for specifying a measurement item which can be measured by the second measurement unit 3 are stored. That is, the first measurement item specifying information 55a is information representing that the CBC+DIFF item including WBC, RBC, PLT, HGB, NEUT, LYMPH, EO, BASO and MONO can be measured by the first measurement unit 2. The second measurement item specifying information 55b is information representing that the NRBC and RET can be measured by the second measurement unit 3 in addition to the above-mentioned CBC+DIFF item. When the samples are allocated to the first measurement unit 2 and the second measurement unit 3, the CPU 51a performs the allocation of the sample using the first measurement item specifying information 55a and the second measurement item specifying information 55b. For example, it can be confirmed that a sample of which the measurement item included in the measurement order is the CBC+DIFF item can be measured by the first measurement unit 2 from the first measurement item specifying information 55a, and also can be measured by the second measurement unit 3 from the second measurement item specifying information 55b. Therefore, the sample is sorted to any one of the first measurement unit 2 and the second measurement unit 3. In addition, when the measurement item included in the measurement order includes the NRBC, it can be confirmed that the sample cannot be measured by the first measurement unit 2 from the first measurement item specifying information 55a but can be measured by the second measurement unit 3 from the second measurement item specifying information 55b. Therefore, the sample is sorted to the second measurement unit 3.

The reading device 51e is composed of a flexible disk drive, a CD-ROM drive, a DVD-ROM drive or the like and can read the computer program or data recorded in a portable recording medium 54. In the portable recording medium 54, the computer program 54a for prompting the computer to function as the information processing unit 5 is stored. The computer 5a can read the computer program 54a from the portable recording medium 54 and install the computer program 54a in the hard disk 51d.

The computer program 54a is provided by the portable recording medium 54 and can also be provided from an external device, which is connected to the computer 5a by an electric communication line (which may be wired or wireless) to communicate therewith, through the electric communication line. For example, the computer program 54a is stored in a hard disk of a server computer on the internet and the computer 5a accesses the server computer to download the computer program and install the computer program in the hard disk 51d.

Furthermore, in the hard disk 51d, for example, a multitasking operating system such as Windows (registered trade name), which is made and distributed by Microsoft corporation in America, is installed. In the following description, the computer program 54a according to this embodiment operates on the above operating system.

The I/O interface 51f is composed of, for example, a serial interface such as USB, IEEE1394 or RS-232C, a parallel interface such as SCSI, IDE or IEEE1284, and an analog interface including a D/A converter and an A/D converter. The input section 53 composed of a keyboard and a mouse is connected to the I/O interface 51f and the user uses the input section 53 so as to input data to the computer 5a. In addition, the I/O interface 51f is connected to the first measurement unit 2, the second measurement unit 3 and the sample transport unit 4. Therefore, the information processing unit 5 can control the first measurement unit 2, the second measurement unit 3 and the sample transport unit 4.

The communication interface 51g is an Ethernet (registered trade name) interface. The communication interface 51g is connected to a host computer 6 via a LAN. Via the communication interface 51g, the computer 5a can send and receive data to and from the host computer 6 connected to the LAN by using a predetermined communication protocol.

The image output interface 51h is connected to the image display section 52 composed of a LCD or a CRT so as to output a picture signal corresponding to the image data provided from the CPU 51a to the image display section 52. The image display section 52 displays an image (screen) in accordance with an input picture signal.

[Operation of Sample Analyzer 1]

Hereinafter, the operation of the sample analyzer 1 according to this embodiment will be described.

<Sample Transport Controlling Process>

Figure 10:
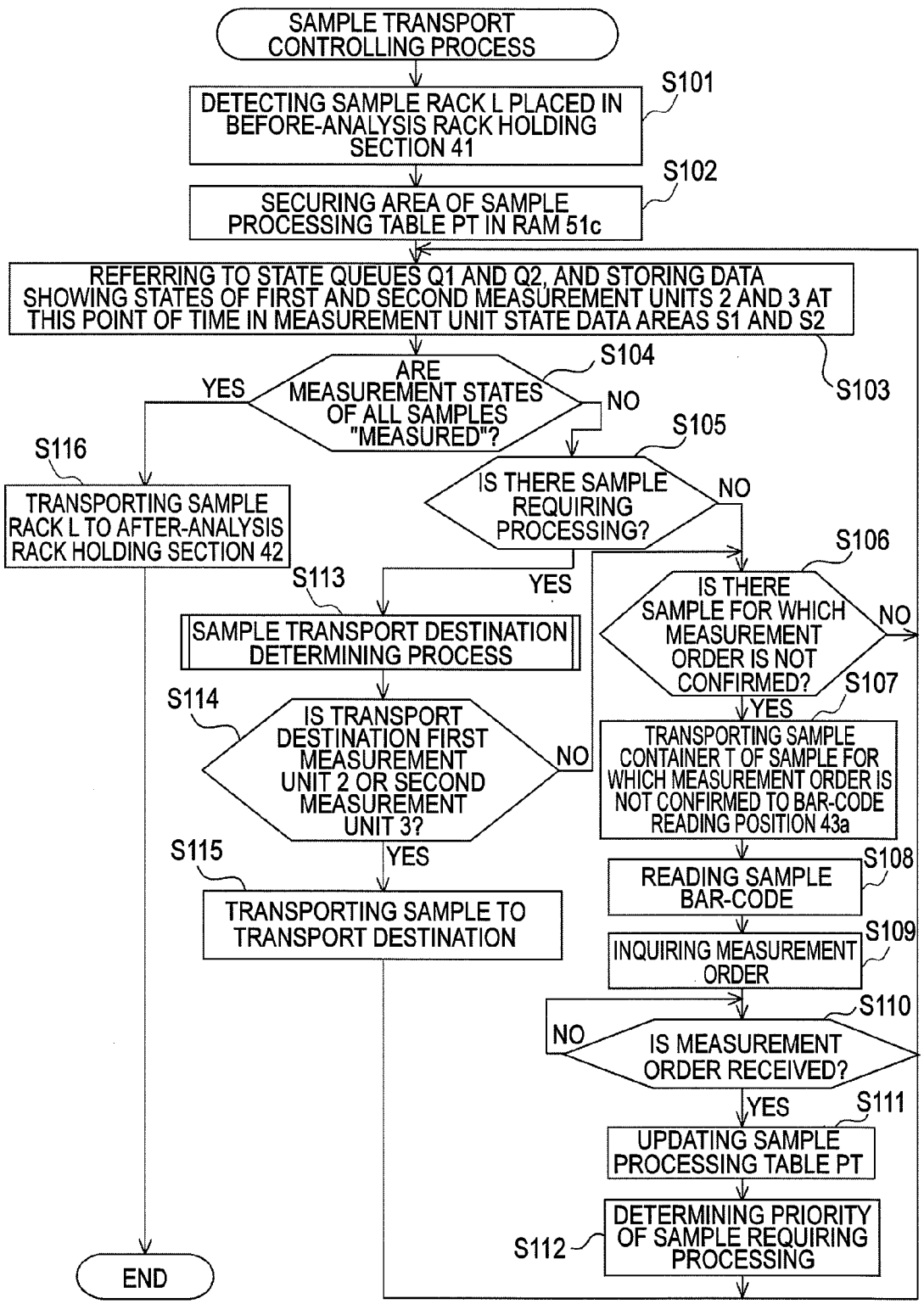
FIG. 10 is a flowchart illustrating the flow of a sample transport controlling process carried out by a CPU of the information processing unit of the sample analyzer according to Embodiment 1.
Figure 11:
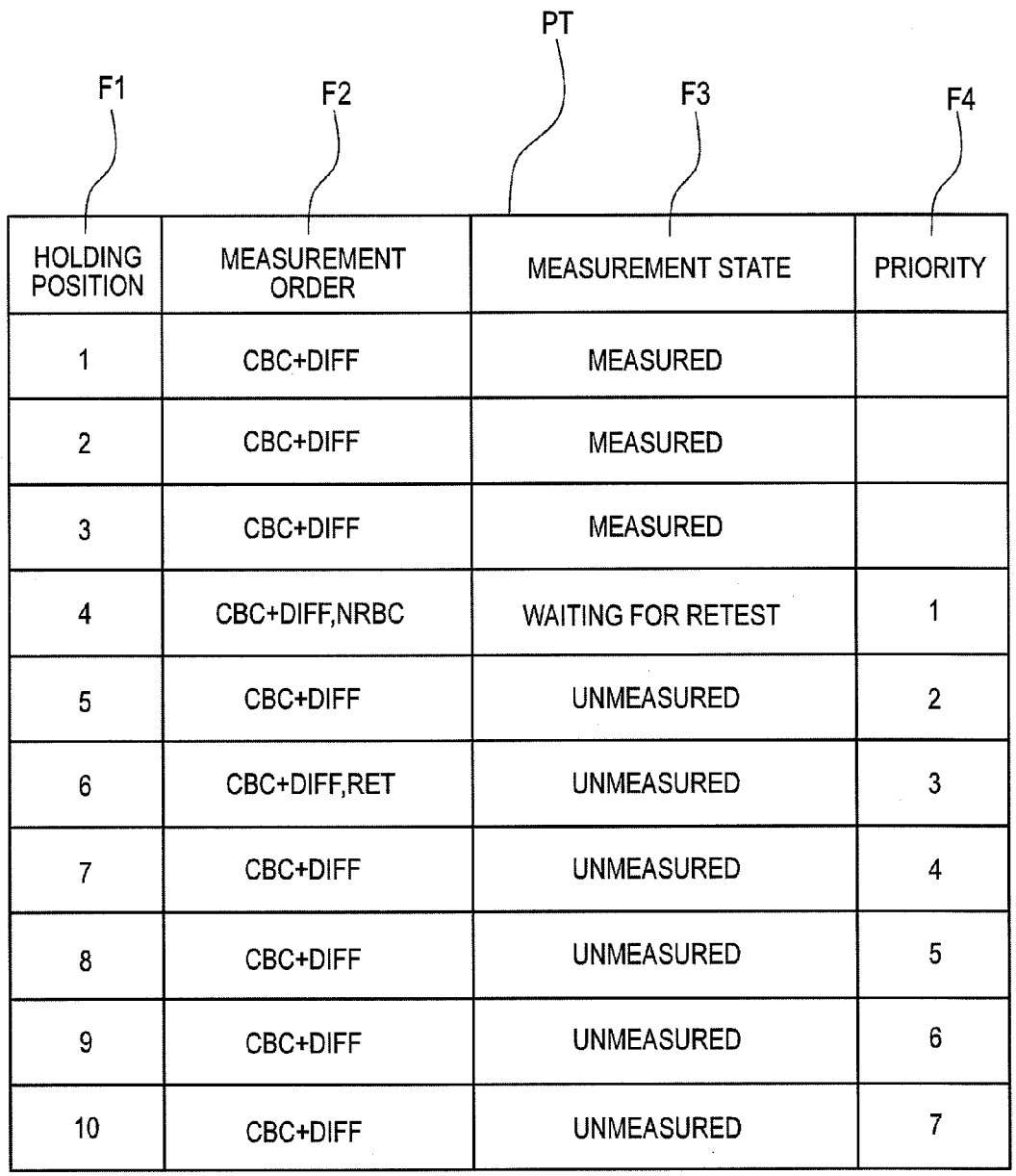
FIG. 11 is a schematic view illustrating the configuration of a sample processing table.

FIG. 10 is a flowchart illustrating the flow of the sample transport controlling process carried out by the information processing unit 5 of the sample processing apparatus 1. An operator places the sample rack L accommodating the plural sample containers T, which contain samples, on the before-analysis rack holding section 41. In this state, the operator operates the input section 53 so as to instruct the information processing unit 5 to perform the sample measuring. The CPU 51a of the information processing unit 5 receives the instruction of performing the sample measuring, and then performs the following sample transport controlling process. First, when detecting the sample rack L which is mounted on the before-analysis rack holding section 41 by a sensor which is not shown in the drawing (Step S101), the CPU 51a secures an area for a sample processing table which is used to measure the sample by the RAM 51c (Step S102). FIG. 11 is a schematic view illustrating the structure of the sample processing table. The sample processing table PT is a table for securing each piece of the information on, such as, the holding position of each sample in the sample rack L, the measurement order, the measurement state of the sample and a measurement priority, for each sample rack L. As shown in FIG. 11, the sample processing table PT is composed of 10 rows, and each row corresponds to the sample which is accommodated in the sample rack L. A field (column) F1 of the holding position of the sample rack L, a field F2 of the measurement order, a field F3 of the measurement state and a field F4 of the priority are provided in the sample processing table PT. In the field F1, information of "1" to "10" representing the holding positions of the sample in the sample rack L is stored. In the field F2, information (information representing the CBC+DIFF item, information representing the CBC+DIFF item and the NRBC etc.) of the measurement item representing the measurement order to be described later is stored. Further, as described above, since the CBC+DIFF item includes each item of WBC, RBC, PLT, HGB, NEUT, LYMPH, EO, BASO, and MONO, the respective pieces of the information of the measurement items may be individually stored in the field F2 and, as shown in FIG. 11, the information representing the "CBC+DIFF" may be stored in the field F2. In the field F3, any one of three types of information, that is, "Unmeasured", "Waiting For Retest" and "Measured" is stored as information representing the measurement state. In the field F4, information of "1" to "10" representing the priority is stored. In Step S102, all the respective cells are in a state of being filled with a blank (NULL is stored) excepting the field F1 of the sample processing table PT.

Next, the CPU 51a refers to the state queues Q1 and Q2 so as to store the data representing the state of the first measurement unit 2 and the second measurement unit 3 at this point of time in the measurement unit state data areas S1 and S2 (Step S103). Here, in the state queues Q1 and Q2, the plural state data may be stored. In this case, the CPU 51a sequentially reads out the state data from the state queues Q1 and Q2, and stores the finally-read data in the measurement unit state data areas 51 and S2. The data which is finally read from the state queues Q1 and Q2 shows the final state of the first measurement unit 2 and the second measurement unit 3, that is, the state of the first measurement unit 2 and the second measurement unit 3 at this point of time. Further, initial values of the state queues Q1 and Q2 are "Sample Loading Possible".

Next, the CPU 51a determines whether or not the measurement state of all the samples is in the state of the "Measured" in the sample processing table PT (Step S104). In Step S104, when there is a sample of which the measurement state is in the state of the "Measured" (NO in Step S104), the CPU 51a determines whether or not there is a sample requiring processing with reference to the sample processing table PT (Step S105). The "Sample requiring processing" indicates a sample which is confirmed regarding the measurement order and is not measured or is waiting for the retest. That is, in the sample processing table PT, a sample in which the information of the measuring data is stored in the field F2 and the information of "Unmeasured" or "Waiting For Retest" is stored in the field F4 corresponds to the "Sample requiring processing". In Step S105, when there is no sample requiring processing (NO in Step S105), the CPU 51a determines whether or not there is a sample in which the measurement order is not confirmed, that is, a sample in which the information of the measurement order is not stored in the field F2 with reference to the sample processing table PT (Step S106).

When there is a sample in which the measurement order is not confirmed in Step S106 (YES in Step S106), the CPU 51a controls the sample transport unit 4 so as to transport the sample rack L. Therefore, among the samples accommodated in the sample rack L, one of the sample containers T of the sample, in which the measurement order is not confirmed, is positioned at the reading position 43d in front of the bar-code reading section 44 (Step S107). Here, as for the sample to be transported at the reading position 43d, among the samples in which the information of the measurement order is not stored in the field F2 of the sample processing table PT, the sample (which is positioned on the most downstream side in the transporting direction of the sample rack L) of which the number of the holding position is smallest is selected. That is, when there is no sample in which the measurement order is not confirmed, a sample of which the holding position is "1" is selected. In addition, when the measurement orders of all the samples excepting the sample of which the holding position is "1" are unconfirmed, a sample of which the holding position is "2" is selected. Therefore, the samples are selected in an order descending from the number of the holding position thereof.

When the selected sample is transported at the reading position 43d, the CPU 51a makes the bar-code reading section 44 read the sample ID from the bar-code of the sample (Step S108), and makes an inquiry to the host computer 6 for the measurement order corresponding to the sample ID (Step S109). This is carried out by transmitting measurement order requirement data including the sample ID to the host computer 6 which is connected via a network. The CPU 51a stands by to receive the measurement order (NO in Step S110). When the measurement order is received (YES in Step S110), the CPU associates the measurement order with the sample ID so as to be stored in the sample processing table PT, so that the sample processing table PT is updated (Step S111).

Next, the CPU 51a determines the priority of the sample requiring processing (Step S112). In this process, the priority of each sample requiring processing is determined according to the following rules. Rule 1: The sample requiring processing in which the RET or NRBC is included in the measurement order as the second measurement item has a priority higher than a sample in which only the CBC+DIFF item is included in the measurement order as the first measurement item. Rule 2: The sample requiring processing on a head side (downstream side in the transporting direction) of the sample rack L has a priority higher than a sample requiring processing on a tail side (upstream side in the transporting direction) of the sample rack L. Further, in Step S112, when there is only one sample requiring processing, the priority of the sample is set to 1 and the priorities of the other samples are not determined. The priorities of the samples as determined above are stored in the sample processing table PT. When the process of Step S112 is completed, the CPU 51a returns the process to Step S103.

Figure 12:
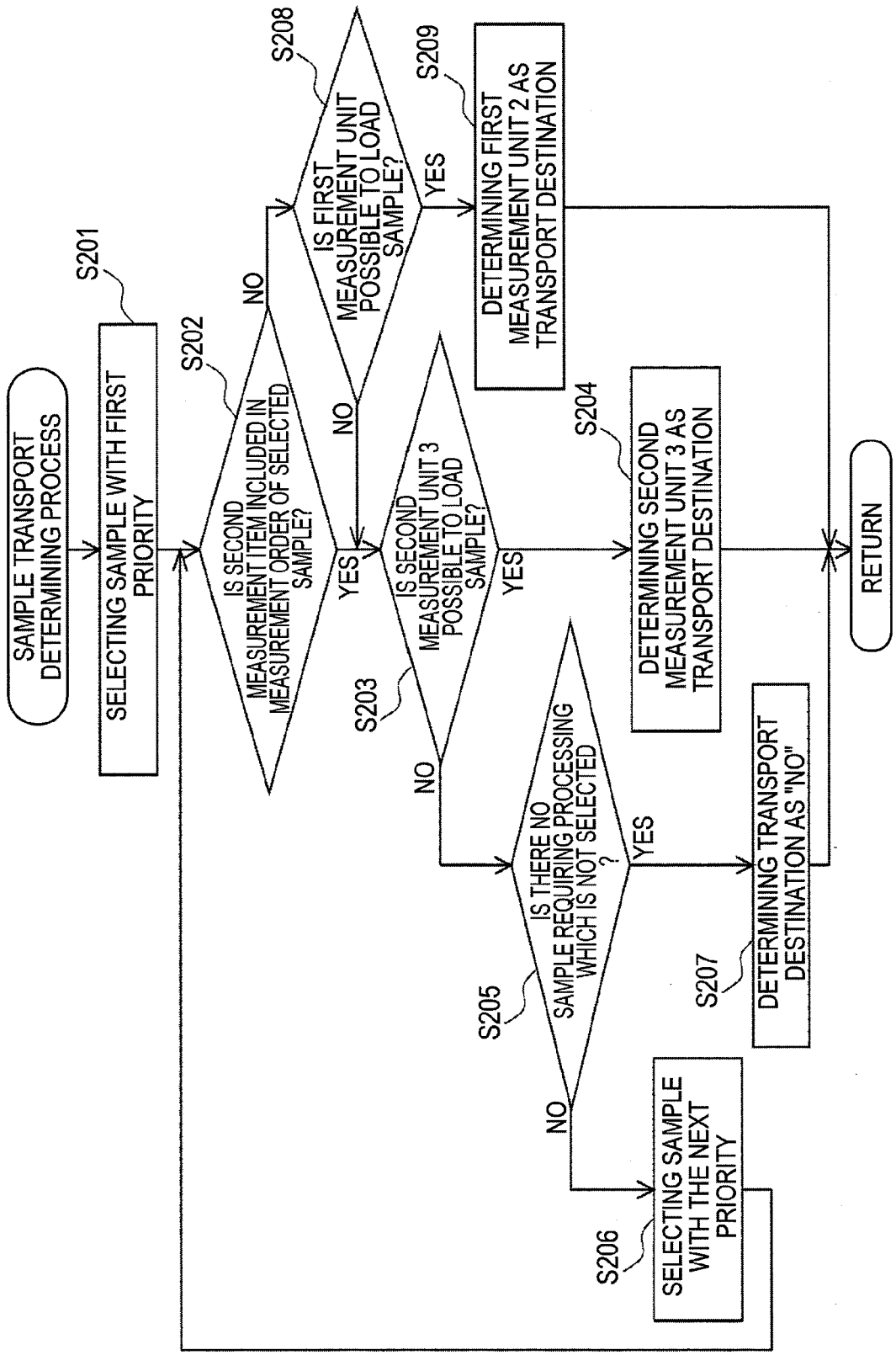
FIG. 12 is a flowchart illustrating the procedure of a sample transport destination determining process carried out by a CPU of the information processing unit of the sample analyzer according to Embodiment 1.

On the other hand, in Step S105 described above, when there is a sample requiring processing (YES in Step S105), the CPU 51a performs the sample transport destination determining process (Step S113). FIG. 12 is a flowchart illustrating the procedure of the sample transport destination determining process. In the sample transport destination determining process, first, the CPU 51a refers to the sample processing table PT so as to select the sample with the first priority (Step S201). Next, the CPU 51a determines whether or not the RET or NRBC item as the second measurement item is included in the measurement order of the selected sample (Step S202).

In Step S202, when the RET or NRBC item is included in the measurement order of the selected sample (YES in Step S202), the CPU 51a refers to the measurement unit state data area S2 of the RAM 51c so as to determine whether or not the state of the second measurement unit 3 is "Sample Loading Possible" (Step S203). In Step S203, when the state of the second measurement unit 3 is "Sample Loading Possible" (YES in Step S203), the CPU 51a determines the second measurement unit 3 as the transport destination (Step S204), and returns the process to an invoked address of the sample transport destination determining process.

On the other hand, in Step S203, when the state of the second measurement unit 3 is "Sample Loading Impossible" (NO in Step S203), the CPU 51a determines whether or not the samples of all the priorities are selected, that is, all the samples requiring processing are selected (Step S205). In Step S205, when there is an unselected sample requiring processing (NO in Step S205), the CPU 51a selects a sample with the next priority (Step S206), and moves the process to Step S202.

In addition, in Step S205, when there is no unselected sample requiring processing (YES in Step S205), the CPU 51a determines that the transport destination is "NO" (Step S207), and returns the process to an invoked address of the sample transport destination determining process.

In Step S202, when the RET or NRBC item is not included in the measurement order of the selected sample (NO in Step S202), the CPU 51a refers to the measurement unit state data area S1 of the RAM 51c so as to determine whether or not the state of the first measurement unit 2 is "Sample Loading Possible" (Step S208). In Step S208, when the state of the first measurement unit 2 is "Sample Loading Possible" (YES in Step S208), the CPU 51a determines the first measurement unit 2 as the transport destination (Step S209), and returns the process to an invoked address of the sample transport destination determining process.

On the other hand, in Step S208, when the state of the first measurement unit 2 is "Sample Loading Impossible" (NO in Step S208), the CPU 51a moves the process to Step S203, and determines whether or not the second measurement unit 3 is in the state where a sample can be loaded.

In this way, when the measurement order of the selected sample includes the first measurement item but not the second measurement item, the state of the first measurement unit 2 is confirmed ahead of the state of the second measurement unit 3. Therefore, when both the first measurement unit 2 and the second measurement unit 3 are in the state where a sample can be loaded, the first measurement unit 2, that is, the measurement unit which cannot measure the second measurement item is selected as the transport destination. Therefore, even though the sample requiring processing to be selected sequentially is a sample in which the measurement order includes the first measurement item and the second measurement item or a sample in which the measurement order includes the first measurement item but not the second measurement item, since the second measurement unit 3 which can measure these samples remains in the state where a sample can be loaded, the second measurement unit 3 can be determined as the transport destination and the process of the sample can be efficiently carried out.

After the sample transport destination determining process as described above, the CPU 51a determines whether the determined transport destination is the first measurement unit 2 or the second measurement unit 3 (Step S114). When the determined transport destination is the first measurement unit 2 or the second measurement unit 3 (YES in Step S114), the CPU transports the selected sample in the sample transport destination determining process to the transport destination (Step S115). Further, in this process, when the transport destination is the first measurement unit 2, the CPU 51a controls the sample transport unit 4 to position the selected sample at the first sample supply position 43a. When the transport destination is the second measurement unit 3, the CPU controls the sample transport unit 4 to position the selected sample at the second sample supply position 43b.

Thereafter, the CPU 51a controls the first measurement unit 2 or the second measurement unit 3 which is determined as the transport destination according to a sample measuring process to be described later so as to carry out loading and measuring on the sample. When the sample measuring process starts, as described later, when the transport destination is the first measurement unit 2, the measurement unit state data area S1 is rewritten with "Sample Loading Impossible". When the transport destination is the second measurement unit 3, the measurement unit state data area S2 is rewritten with "Sample Loading Impossible". In order to remove the selected sample from the samples requiring processing, the measurement state of the selected sample in the sample processing table PT is changed to "Measured", so that the sample processing table PT is updated. After the process of Step S115 as described above is completed, the CPU 51a returns the process to Step S103.

On the other hand, in Step S114, when the transport destination determined by the sample transport destination determining process is "NO" (NO in Step S114), the CPU 51a moves the process to Step S106, refers to the sample processing table PT so as to determine whether or not there is a sample in which the measurement order is not confirmed (Step S106).

In addition, in Step S106, when there is a sample in which the measurement order is not confirmed (NO in Step S106), the CPU 51a moves the process to Step S103, refers to the state queues Q1 and Q2 so as to store data representing the state of the first measurement unit 2 and the second measurement unit 3 at this point of time in the measurement unit state date areas S1 and S2 (Step S103).

In Step S104, when the measurement states of all the samples are "Measured" in the sample processing table PT (YES in Step S104), the CPU 51a controls the sample transport unit 4 to transport the sample rack L to the after-analysis rack holding section 42 by the rack transport section 43 (Step S116), and completes the process. Thereafter, when a sample rack L is further placed at the after-analysis rack holding section 41 and the sample rack L is detected by a sensor, the CPU 51a performs the subsequent processes of Step S101 again. Therefore, the transport process is carried out in the samples until all the sample racks L placed at the before-analysis rack holding section 41 are completely processed.

<Sample Measuring Process>

Figure 13:
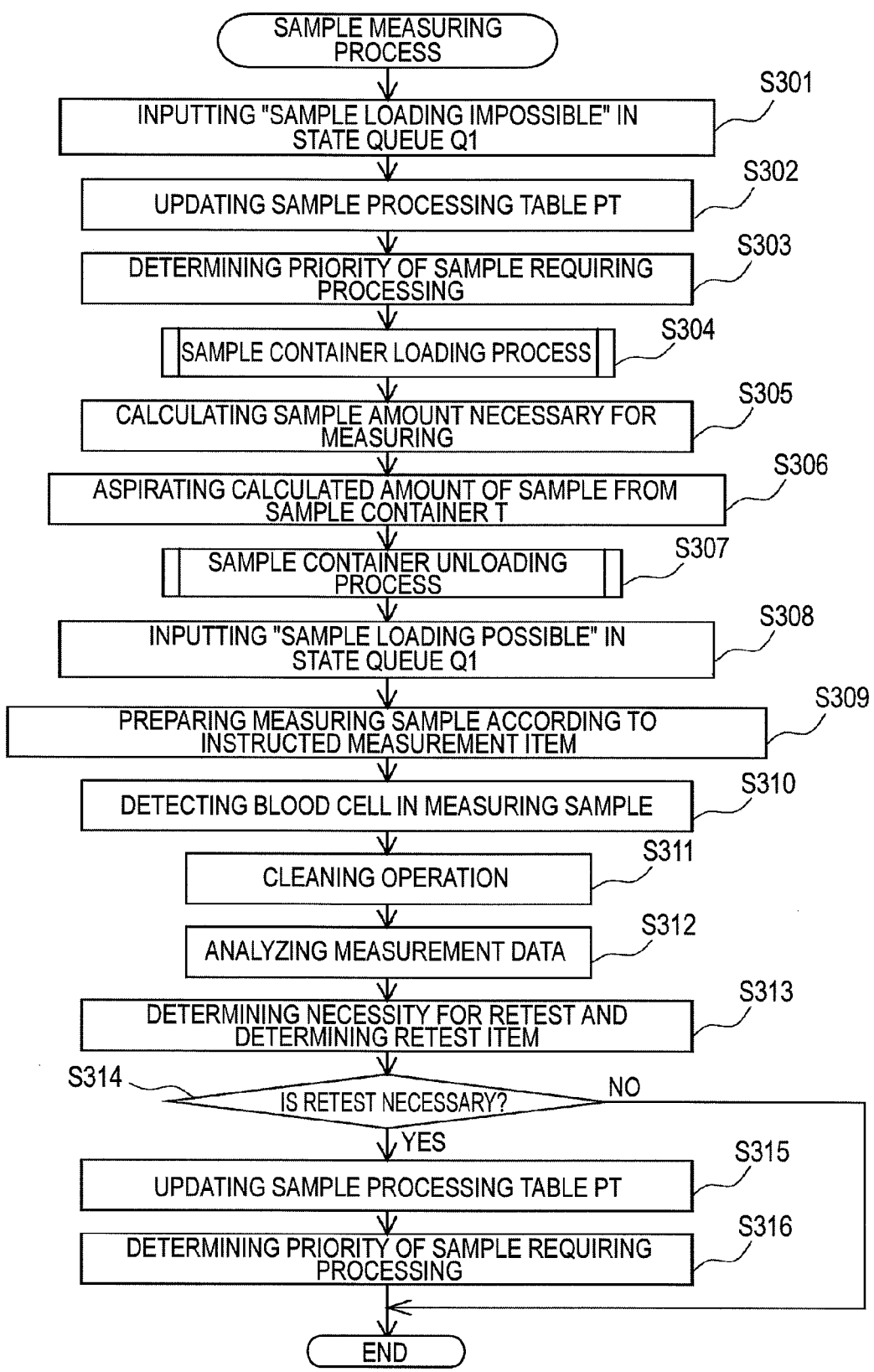
FIG. 13 is a flowchart illustrating the flow of a sample measuring process carried out by a CPU of the information processing unit of the sample analyzer according to Embodiment 1.

Next, the sample measuring process carried by the information processing unit 5 will be described. FIG. 13 is a flowchart illustrating the flow of the sample measuring process carried by the information processing unit 5 of the sample analyzer 1.

When the measurement unit state data area S1 is "Sample Loading Possible" and the sample container T is detected at the first sample supply position 43a by the sample container sensor 45a, the CPU 51a performs the sample measuring process by the first measurement unit 2. On the other hand, when the measurement unit state date area S2 is "Sample Loading Possible" and the sample container T is detected at the second sample supply position 43b by the sample container sensor 45b, the CPU 51a performs the sample measuring process by the second measurement unit 3. Further, here, the sample measuring process carried out by the first measurement unit 2 will be described.

In the measurement process carried out by the first measurement unit 2, first, the CPU 51a inputs "Sample Loading Impossible" in the state queue Q1 of the RAM 51c (Step S301). In addition, the CPU 51a changes the measurement state of the sample in the sample processing table PT to "Measured" in order to remove the sample from the samples requiring processing, so that the sample processing table PT is updated (Step S302). Furthermore, the CPU 51a performs a priority determining process on the samples requiring processing as described in Step S112 (Step S303).

Figure 14:
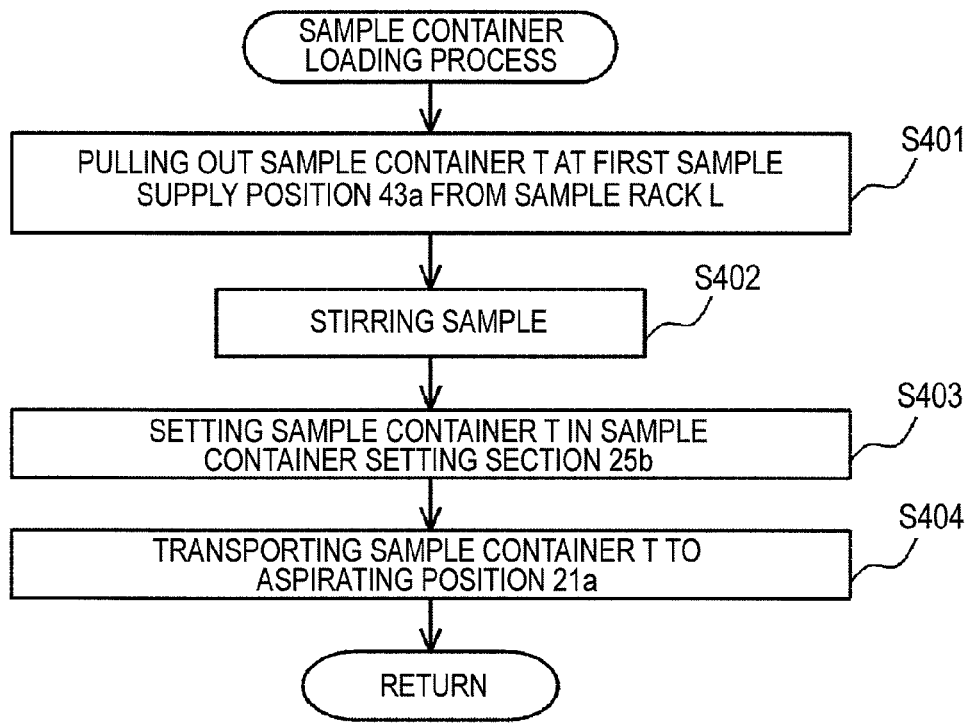
FIG. 14 is a flowchart illustrating the procedure of a sample container loading process carried out by a CPU of the information processing unit of the sample analyzer according to Embodiment 1.

Next, the CPU 51a performs a sample container loading process in which the sample container T at the first sample supply position 43a is loaded into the first measurement unit 2 (Step S304). FIG. 14 is a flowchart illustrating the procedure of the sample container loading process carried out by the CPU 51a of the information processing unit 5. First, the CPU 51a controls the sample container transport section 25 so as to pull out the sample container T at the first sample supply position 43a from the sample rack L (Step S401), and controls the hand section 25a to oscillate the sample container T so as to stir the sample therein (Step S402). Next, the CPU 51a controls the hand section 25a to set the sample container T on the sample container setting section 25b (Step S403), and further controls the sample container transport section 25 to transport the sample container T to the aspirating position 21a (Step S404). After the process of Step S404 is completed, the CPU 51a returns the process to an invoked address of the sample container loading process.

Figure 15:
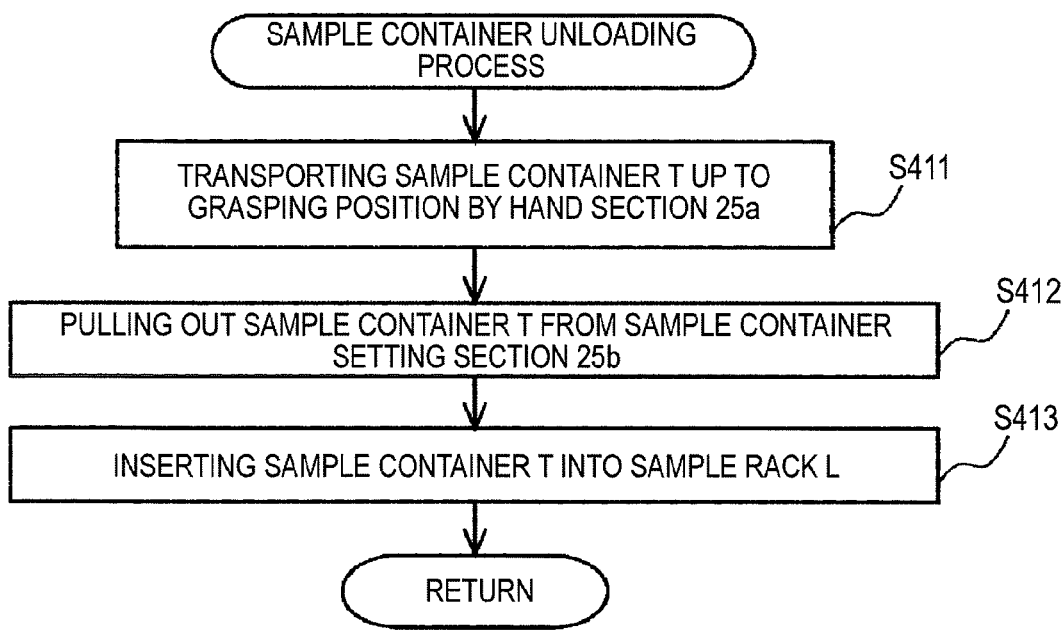
FIG. 15 is a flowchart illustrating the procedure of a sample container unloading process carried out by a CPU of the information processing unit of the sample analyzer according to Embodiment 1.

Returning to FIG. 13, after the sample container loading process S304, the CPU 51a refers to the measurement order of the sample so as to calculate a sample amount required for measuring the measurement item (Step S305). Next, the CPU 51a controls the sample aspirating section 21 so as to aspirate the sample by the amount required for measuring from the sample container T (Step S306). After the aspiration of the sample is completed, the CPU 51a performs the sample container unloading process in which the loaded sample container T returns to the first sample supply position 43a (Step S307). FIG. 15 is a flowchart illustrating the procedure of the sample container unloading process carried out by the CPU 51a of the information processing unit 5. First, the CPU 51a controls the sample container transport section 25 and moves the sample container setting section 25b from the aspirating position to be transported up to a position where the sample container T can be grasped by the hand section 25a (Step S411). Next, the CPU 51a controls the hand section 25a so as to grasp the sample container T by the hand section 25a, and then pulls out the sample container T from the sample container setting section 25b (Step S412). Furthermore, the CPU 51a controls the hand section 25a so as to insert the grasped sample container T to the holding position of the sample rack L of the first sample supply position 43a (Step S413). After the process of Step S413 is completed, the CPU 51a returns the process to an invoked address of the sample container unloading process.

Returning to FIG. 13, after the sample container unloading process of S307 is completed, the first measurement unit 2 becomes in a state where a sample can be loaded, the CPU 51a inputs "Sample Loading Possible" in the state queue Q1 of the RAM 51c (Step S308).

Next, the CPU 51a controls the sample preparing section 22 so as to prepare a measuring sample corresponding to the measurement item (Step S309). Then, the CPU supplies the measuring reagent to the detecting section 23 so as to carry out the detection of the blood cell in the measuring reagent by the detecting section 23 (Step S310). Therefore, the CPU 51a obtains measurement data output from the detecting section 23. Thereafter, the CPU 51a performs a cleaning operation for cleaning a flow path used for the measurement and a reaction chamber (Step S311).

In addition, the CPU 51a performs an analysis process of the measurement data (Step S312) so as to obtain the analysis result regarding each measurement item included in the measurement order, such as, the numerical values of RBC, PLT, HGB, WBC, NEUT, LYMPH, EO, BASO and MONO. After the process of Step S312 is completed, the CPU 51a determines whether or not the retest (remeasurement) of the sample is necessary. When the retest is necessary, the CPU 51a determines the measurement item (hereinafter, referred to as "retest item") relating to the retest (Step S313). For example, in the process, when the CBC+DIFF item is measured, it is determined that the retest is not necessary when the number of the white blood cells (WBC) falls within a first numerical range (normal range). In addition, when the numerical value of the WBC exceeds the first numerical range and falls within a second numerical range, it is determined that the retest is necessary and the retest item is determined as the CBC+DIFF item which is the same as that of a first-round test. Furthermore, when the numerical value of the WBC exceeds the second numerical range, it is determined that the retest is necessary and the retest item is determined as the CBC+DIFF item and the NRBC.

After the process of Step S313, the CPU 51a determines whether or not it is determined that the retest is necessary (Step S314). When it is determined that the retest is necessary (YES in Step S314), the CPU 51a updates the sample processing table PT (Step S315). In the process of Step S315, the CPU 51a rewrites data of the measurement order of the sample with the retest item which is determined in the process of Step S313, and rewrites the data of the measurement state with "Waiting For Retest". Therefore, since the sample becomes a necessity-for-retest sample, the CPU 51a performs the priority determining process on the samples requiring processing as described in Step S112 (Step S316), and completes the subsequent processes.

On the other hand, when it is determined that the retest is not necessary (NO in Step S314), the CPU 51a completes the process.

Further, the sample measuring process carried out by the second measurement unit 3 is the same as the sample measuring process carried out by the first measurement unit 2 excepting that the second measurement items of NRBC and RET can be measured, so that the description thereof will be omitted.

Figure 16:
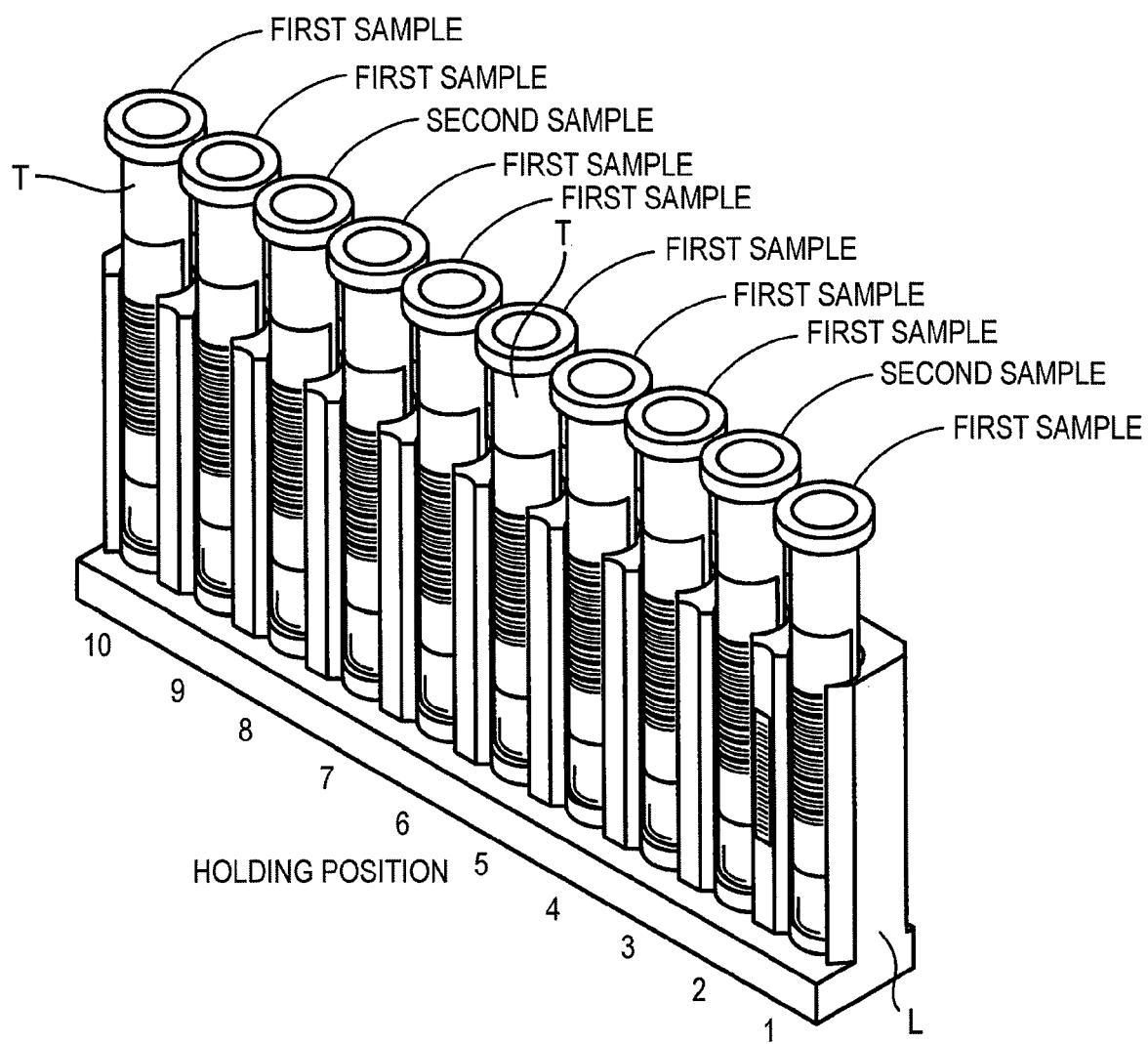
FIG. 16 is a perspective view illustrating an example of a sample rack holding sample containers which contain various samples.

Next, using a specific example where a sample in which the measurement item includes the CBC+DIFF item as the first measurement item but not the NRBC and RET as the second measurement item (hereinafter, referred to as "a first sample") and a sample in which the measurement item includes the CBC+DIFF item as the first measurement item and the NRBC as the second measurement item (hereinafter, referred to as "a second sample) are mixed, the operation of the above-mentioned sample analyzer 1 will be described. In the following, as shown in FIG. 16, the operation of the sample analyzer 1 will be described in a case where the sample rack L is loaded in the sample analyzer 1, where the first samples are held on the holding positions 1, 3, 4, 5, 6, 7, 9, and 10 and the second samples are held on the holding positions 2 and 8.

Figure 17:
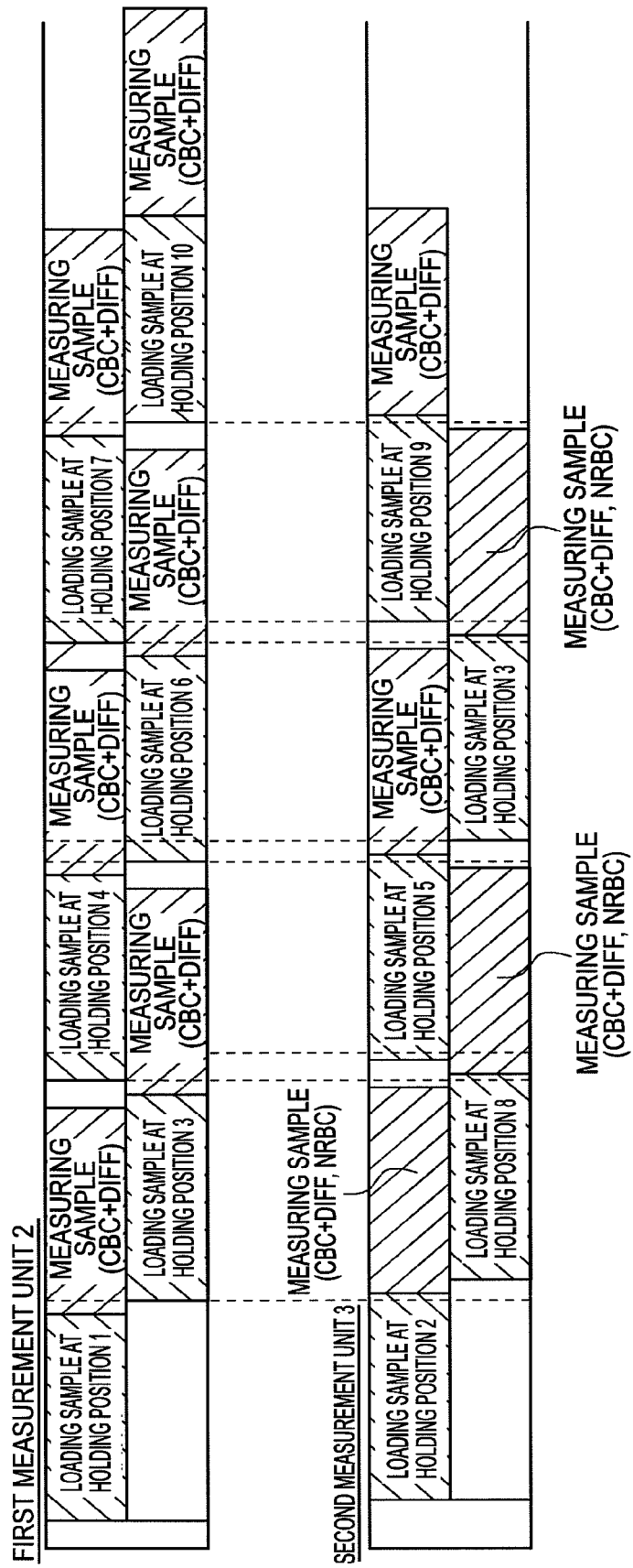
FIG. 17 is a timing chart illustrating the operation of a first measurement unit and a second measurement unit of the sample analyzer when a sample rack is put into the sample analyzer.

FIG. 17 is a timing chart illustrating the operation of the first measurement unit 2 and the second measurement unit 3 of the sample analyzer 1 when the sample rack L is loaded in the sample analyzer 1. Further, "Sample Loading" shown in FIG. 17 corresponds to the processes of Steps S301 to S307, and in the following description, the processes of Steps S301 to S307 are referred to as a "sample loading process". In addition, "Sample Measurement" shown in FIG. 17 corresponds to the processes of Steps S308 to S316.

Figure 18A:
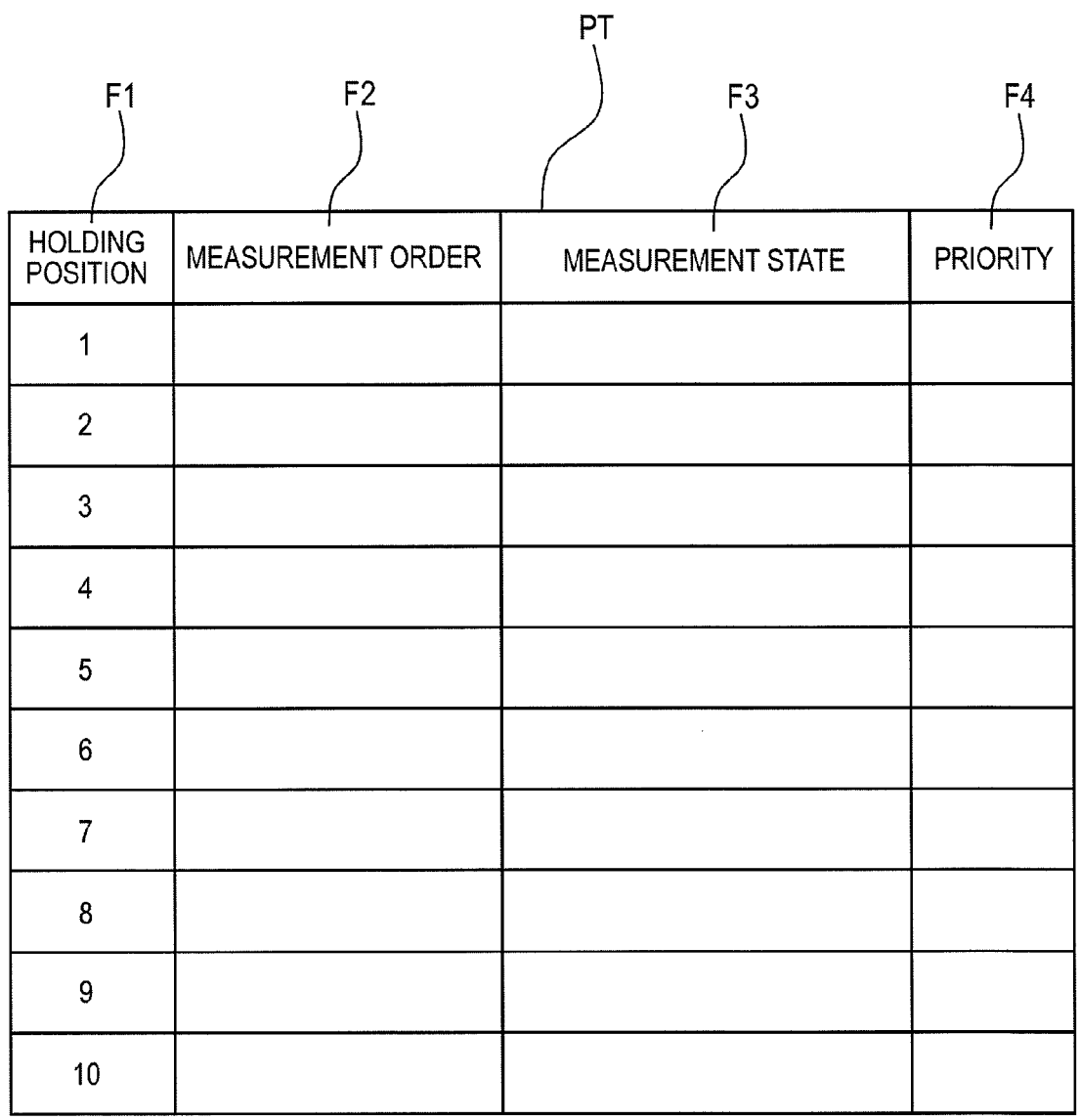
FIG. 18A is a diagram schematically illustrating an example of a state of the sample processing table.

First, when the sample rack L is loaded in the before-analysis rack holding section 41 and an operator instructs the information processing unit 5 to perform the sample measurement, the sample rack L placed on the before-analysis rack holding section 41 is detected (Step S101 shown in FIG. 10) and an area for the sample processing table PT is secured in the information processing unit 5 (Step S102). FIGS. 18A to 18I are diagrams illustrating the states of the sample processing table PT. The state of the sample processing table PT at this point of time is shown in FIG. 18A. At this point of time, the sample processing table PT is in a state where all the cells are registered with no data.

Next, the state queues Q1 and Q2 are referred by the CPU 51a, and the data recently input in each of the state queues Q1 and Q2 is stored in the measurement unit state data areas S1 and S2 (Step S103). Here, since both the state queues Q1 and Q2 are input with "Sample Loading Possible" as the initial values, "Sample Loading Possible" is stored in each of the measurement unit state data areas S1 and S2.

Next, the CPU 51a determines whether or not the measurement states of all the samples are "Measured" in the sample processing table PT (Step S104). However, since there is no one in which the data of "Measured" is registered at the field F3 of the measurement state in the sample processing table PT (NO in Step S104), the process of the CPU 51a proceeds to Step S105. In addition, in Step S105, it is determined whether or not there is a sample requiring processing. However, since there is no sample requiring processing in the sample processing table PT (NO in Step S105), the process of the CPU 51a proceeds to Step S106.

Next, the CPU 51a determines whether or not there is a sample in which the measurement order is not confirmed (Step S106). Here, in the sample processing table PT, there is no record in which information of the measurement order is stored in the field F2 of the measurement order. That is, there are only the samples in which the measurement order is not confirmed (NO in Step S106). Therefore, the process of the CPU 51a proceeds to Step S107.

Figure 18B:
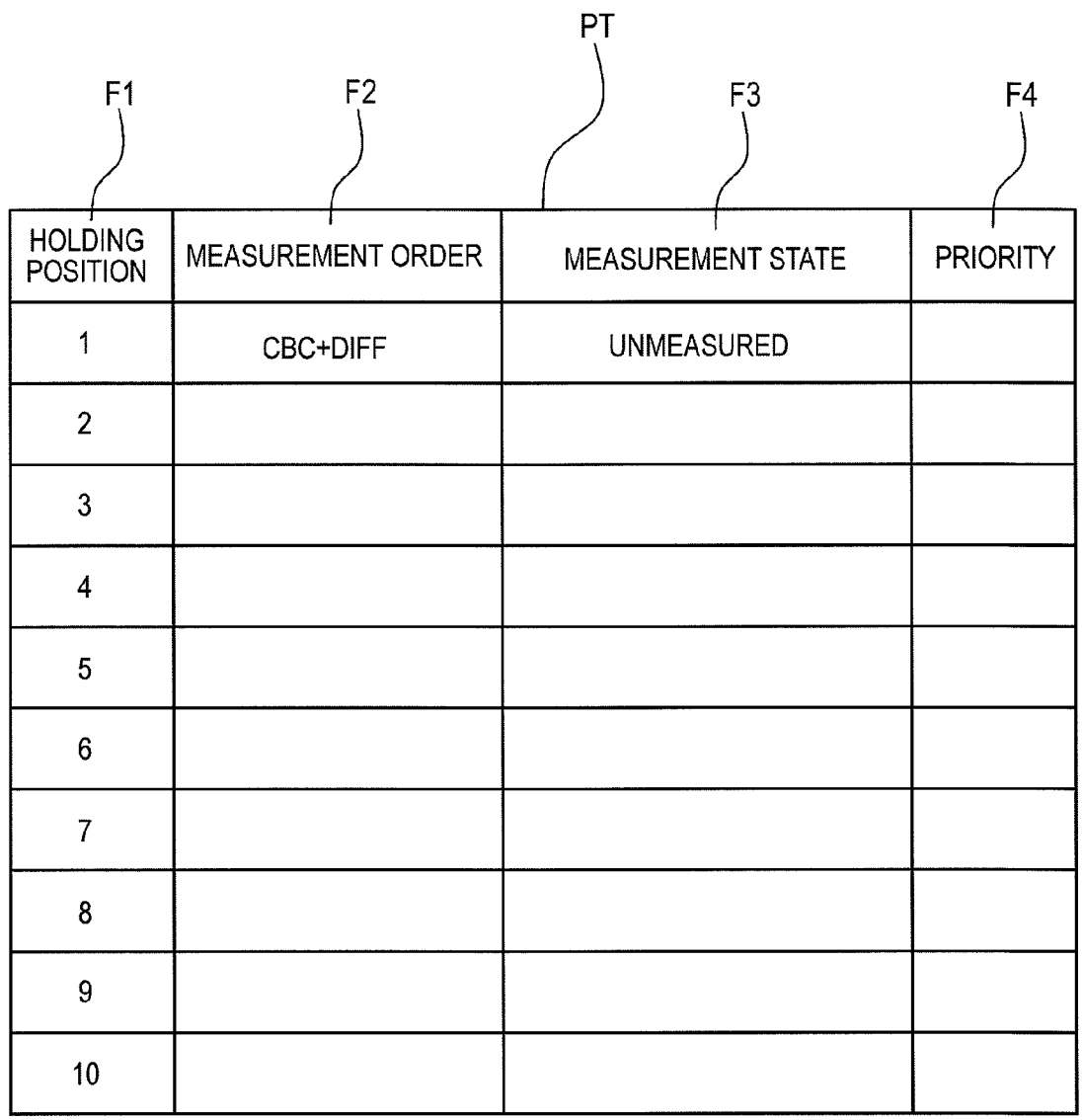
FIG. 18B is a diagram schematically illustrating an example of a state of the sample processing table.

Next, one of the sample containers T accommodated in the sample rack L, in which the measurement order is not confirmed, is transported up to the reading position 43d in front of the bar-code reading section 44 (Step S107). Here, since there is no sample in which the measurement order is confirmed at all, the sample at the holding position 1 is transported up to the holding position 43d. Next, the sample ID is read by the bar-code reading section 44 from the bar-code of the sample at the holding position 1 (Step S108). The measurement order of the sample at the holding position 1, that is, the measurement order which includes the CBC+DIFF item but not the second measurement item is obtained from the host computer 6 by the CPU 51a (Steps S109 and S110). Then, the sample processing table PT is updated (Step S111). The state of the sample processing table PT at this point of time is shown in FIG. 18B. As shown in the drawing, at this point of time, the information representing the "CBC+DIFF" is stored in the field F2 of the measurement order, and the information representing the "Unmeasured" is stored in the field F3 of the measurement state in the raw of the holding position 1 of the sample processing table PT.

Next, the CPU 51a determines the priorities of the samples requiring processing (Step S112). Here, since only information relating to a sample at the holding position 1 is stored in the sample processing table PT and only the sample corresponds to the sample requiring processing, the priority of the sample is determined as the first priority. In addition, in the sample processing table PT, the information representing "1" is stored in the field F4 of the priority of the sample at the holding position 1.

The CPU 51a performs the process of Step S103 again. The CPU 51a refers to the state queues Q1 and Q2, and the finally input data in the state queues Q1 and Q2 is stored in the measurement unit state data areas S1 and S2 (Step S103). Here, since there is no data in the state queues Q1 and Q2, the data of the measurement unit state data areas S1 and S2 is not changed. That is, "Sample Loading Possible" is stored in each of the measurement unit state data areas S1 and S2.

Next, the process of Step S104 is performed. Since there is no record in which the data of "Measured" is registered at the field F3 of the measurement state in the sample processing table PT (NO in Step S104), it is determined whether or not there is a sample requiring processing in Step S105. Here, the sample at the holding position 1 is the sample requiring processing because there is information on the measurement order in the sample processing table PT and the measurement state is "Unmeasured". Therefore, the sample transport destination determining process S113 is performed by the CPU 51a.

In the sample transport destination determining process, first, the sample at the holding position 1 as the sample with the first priority is selected in the sample processing table PT by the CPU 51a (Step S201), and it is determined whether or not the second measurement item is included in the measurement order of the sample (Step S202). Here, since the sample at the holding position 1 is the first sample and the second measurement item is not included in the measurement order (NO in Step S202), it is determined whether or not the first measurement unit 2 is in a state where a sample can be loaded from the measurement unit state data area S1 of the RAM 51c (Step S208). Here, the information of "Sample Loading Possible" is stored in the measurement unit state data areas S1 and S2. Therefore, it is determined that the first measurement unit 2 can load the sample (YES in Step S208), the first measurement unit 2 is determined as the transport destination (Step S209), and the process is returned to an invoked address of the sample transport destination determining process S112.

Next, the CPU 51a determines whether the determined transport destination is the first measurement unit 2 or the second measurement unit 3 (Step S114). Since the transport destination is determined as the first measurement unit 2 (YES in Step S114), the sample at the holding position 1 is transported to the first sample supply position 43a (Step S115).

Here, since the measurement unit state data area S1 is "Sample Loading Possible" and the sample container T at the first sample supply position 43a is detected by the sample container sensor 45a, the CPU 51a urges the first measurement unit 2 to perform the sample measuring process. When the sample measuring process starts, "Sample Loading Impossible" is input to the state queue Q1 (Step S301), the measurement state of the sample at the holding position 1 in the sample processing table PT is rewritten with "Measured" (Step S302). In addition, since the sample at the holding position 1 is removed from the samples requiring processing, the information of priority of the sample in the sample processing table PT is deleted (Step S303). The state of the sample processing table PT at this point of time is shown in FIG. 18C.

Next, the sample container loading process is performed by the CPU 51a (Step S304), the sample container T at the holding position 1 is pulled out from the sample rack L and loaded into the first measurement unit 2 (Steps S401 to S404).

Even though the sample container T at the holding position 1 is in a state of being pulled out, the sample rack L can be transported. Here, the CPU 51a performs the subsequent processes of Step S103 again while the sample loading process is being performed. At the point of time, since the finally input data in the state queue Q1 is "Sample Loading Impossible", the information of "Sample Loading Impossible" is stored in the measurement unit state data area S1 (Step S103). In addition, as shown in FIG. 18C, since the measurement state of the sample excepting the one at the holding position 1 are not "Measured" (NO in Step S104) and there is no sample requiring processing (NO in Step S105) and there is a sample in which the measurement order is not confirmed (YES in Step S106), the sample bar-code of the sample at the holding position 2 is read (Steps S107 and S108) and the measurement order of the sample is obtained by the CPU 51a (Steps S109 and S110). Here, the sample at the holding position 2 is the second sample, and the measurement order includes the NRBC in addition to the CBC+DIFF item. In addition, the information representing "CBC+DIFF, NRBC" is stored in the field F2 of the measurement order in the row at the holding position 2 in the sample processing table PT, and the information representing "Unmeasured" is stored in the field F3 of the measurement state (Step S111). Furthermore, since only the sample at the holding position 2 corresponds to the sample requiring processing, the priority of the sample is determined as the first priority, and the information representing "1" is stored in the field F4 of the priority of the sample at the holding position 2 in the sample processing table PT (Step S112). The state of the sample processing table PT at this point of time is shown in FIG. 18D.

Even though the process of Step S103 is performed again by the CPU 51a, since there is no data in the state queues Q1 and Q2 at this point of time, the data of the measurement unit state data areas S1 and S2 are not changed. That is, "Sample Loading Impossible" is stored in the measurement unit state data area S1, and "Sample Loading Possible" is stored in the measurement unit state data area S2.

In addition, as shown in FIG. 18D, since the measurement states of the samples excepting the one at the holding position 1 are not "Measured" (NO in Step S104), it is determined whether or not there is a sample requiring processing in Step S105. Here, since there is information on the measurement order in the sample processing table PT and the measurement state is "Unmeasured", the sample at the holding position 2 is the sample requiring processing. Therefore, the sample transport destination determining process S113 is performed by the CPU 51a.

In the sample transport destination determining process, first, the sample at the holding position 2 as the sample with the first priority is selected in the sample processing table PT by the CPU 51a (Step S201), and it is determined whether or not the second measurement item is included in the measurement order of the sample (Step S202). Here, since the sample at the holding position 2 is the second sample and the second measurement item is not included in the measurement order (YES in Step S202), it is determined whether or not the second measurement unit 3 is in a state where a sample can be loaded from the measurement unit state data area S2 of the RAM 51c (Step S203). At this point of time, the information of "Sample Loading Possible" is stored in the measurement unit state data area S2. Therefore, it is determined that the second measurement unit 3 can load the sample (YES in Step S203), the second measurement unit 3 is determined as the transport destination (Step S204), and the process is returned to an invoked address of the sample transport destination determining process S113.

Next, the CPU 51a determines whether the determined transport destination is the first measurement unit 2 or the second measurement unit 3 (Step S114). Since the transport destination is determined as the second measurement unit 3 (YES in Step S114), the sample at the holding position 2 is transported to the second sample supply position 43b (Step S115).

Here, since the measurement unit state data area S2 is "Sample Loading Possible" and the sample container T at the second supply position 43b is detected by the sample container sensor 45b, the CPU 51a urges the second measurement unit 3 to perform the sample measuring process. When the sample measuring process starts, "Sample Loading Impossible" is input to the state queue Q2 (Step S301), the measurement state of the sample at the holding position 2 in the sample processing table PT is rewritten with "Measured"

Figure 18E:
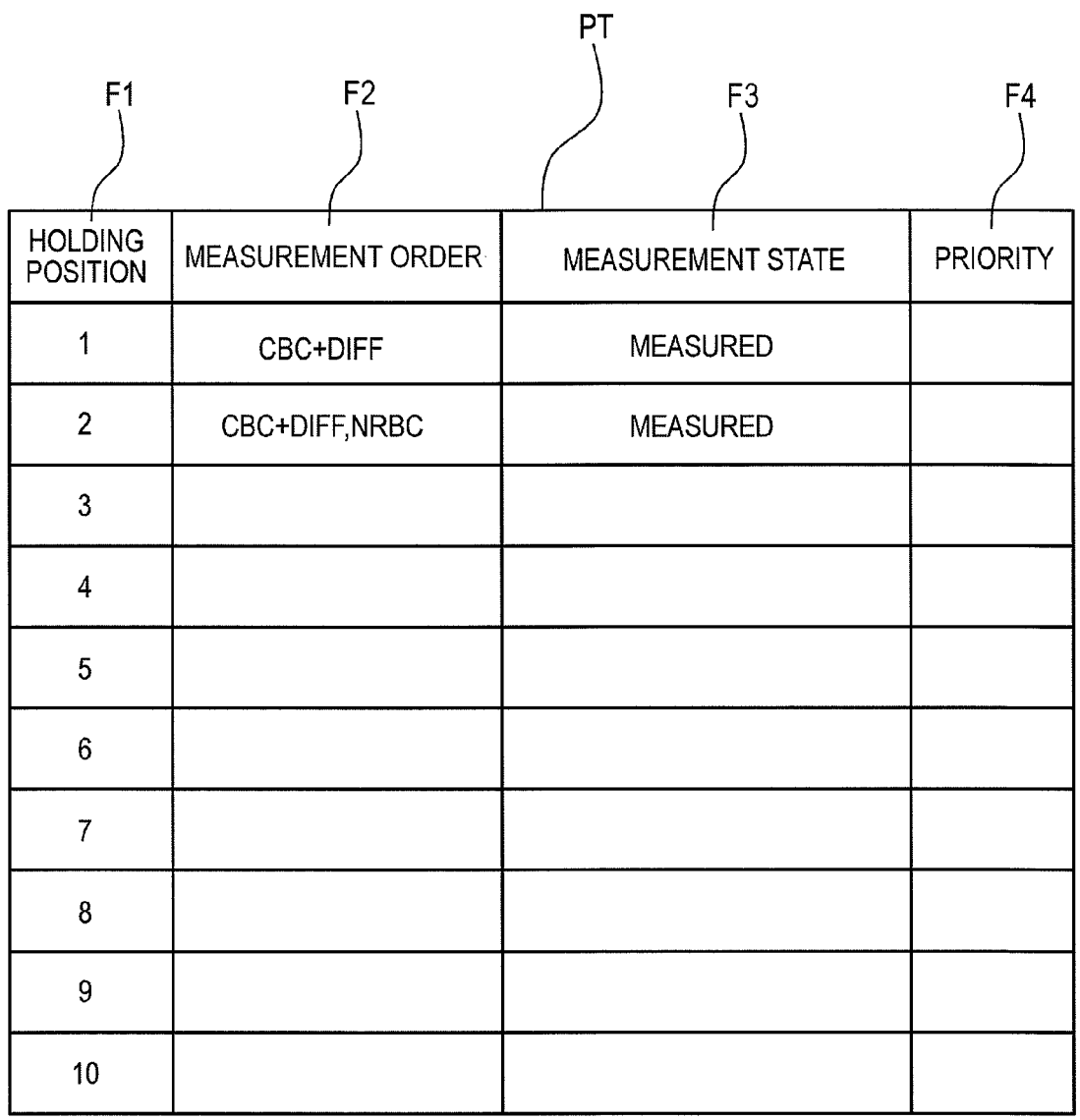
FIG. 18E is a diagram schematically illustrating an example of a state of the sample processing table.

(Step S302). In addition, since the sample at the holding position 2 is removed from the samples requiring processing, the information of priority of the sample in the sample processing table PT is deleted (Step S303). The state of the sample processing table PT at this point of time is shown in FIG. 18E.

Next, the sample container loading process is performed by the CPU 51a (Step S304), the sample container T at the holding position 2 is pulled out from the sample rack L and loaded into the second measurement unit 3 similarly to above-mentioned the sample container T at the holding position 1 (Steps S401 to S404). Further, as shown in FIG. 17, the sample loading process of the sample container T at the holding position 1 as described above is also performed in parallel.

It takes about tens of seconds from the loading of the above-mentioned sample container T to the unloading of the sample container T. The CPU 51a performs the sample transport controlling process while the above-mentioned sample loading process is being performed on the samples at the holding positions 1 and 2.

The CPU 51a performs the subsequent processes of Step S103 again when the sample loading process is performed by the first measurement unit 2 and the second measurement unit 3. At the point of time, since the finally input data in the state queue Q2 is "Sample Loading Impossible", the information of "Sample Loading Impossible" is stored in the measurement unit state data area S2. On the other hand, since no data is input in the state queue Q1, the data stored in the measurement unit state data area S1 remains in "Sample Loading Impossible", and is not changed (Step S103).

As shown in FIG. 18E, since the measurement states of the samples at the holding positions 3 to 10 are not "Measured" (NO in Step S104) and there is no sample requiring processing (NO in Step S105) and the measurement orders of the samples at the holding positions 3 to 10 are not confirmed (YES in Step S106), the sample bar-code of the sample at the holding position 3 is read (Steps S107 and S108) and the measurement order of the sample is obtained by the CPU 51a (Steps S109 and S110). Here, the sample at the holding position 3 is the first sample, and the measurement order includes the CBC+DIFF item but not the second measurement item. Therefore, the information representing "CBC+DIFF" is stored in the field F2 of the measurement order in the row at the holding position 3 in the sample processing table PT, and the information representing "Unmeasured" is stored in the field F3 of the measurement state (Step S111). Furthermore, since only the sample at the holding position 3 corresponds to the sample requiring processing, the priority of the sample is determined as the first priority, and the information representing "1" is stored in the field F4 of the priority of the sample at the holding position 3 in the sample processing table PT (Step S112). The state of the sample processing table PT at this point of time is shown in FIG. 18F.

The CPU 51a performs the process of Step S103 again. At the point of time, since there is no data in the state queues Q1 and Q2, the data of the measurement unit state data areas S1 and S2 is not changed in the process of Step S103. That is, "Sample Loading Impossible" is stored in each of the measurement unit state data areas S1 and S2.

In addition, as shown in FIG. 18F, since the measurement states of the samples at the holding positions 3 to 10 are not "Measured" (NO in Step S104), it is determined whether or not there is a sample requiring processing in Step S105. Here, since there is information on the measurement order in the sample processing table PT and the measurement state is "Unmeasured", the sample at the holding position 3 is the sample requiring processing. Therefore, the sample transport destination determining process S113 is performed by the CPU 51a.

In the sample transport destination determining process, first, the sample at the holding position 3 as the sample with the first priority is selected in the sample processing table PT by the CPU 51a (Step S201), and it is determined whether or not the second measurement item is included in the measurement order of the sample (Step S202). Here, since the sample at the holding position 2 is the first sample and the second measurement item is not included in the measurement order (NO in Step S202), it is determined whether or not the first measurement unit 2 is in a state where a sample can be loaded from the measurement unit state data area 51 of the RAM 51c (Step S208). At this point of time, the information of "Sample Loading Impossible" is stored in the measurement unit state data areas S1. Therefore, it is determined that the first measurement unit 2 cannot load the sample (NO in Step S208). Next, it is determined whether or not the second measurement unit 3 is in a state where the sample can be loaded from the measurement unit state data area S2 of the RAM 51c (Step S203). At this point of time, the information of "Sample Loading Impossible" is stored in the measurement unit state data area S2. Therefore, the CPU determines that the second measurement unit 3 cannot load the sample (NO in Step S203).

Next, the CPU 51a determines whether or not the samples of all the priorities are selected (Step S205). As shown in FIG. 18F, since the sample of which the priority is set is only the sample at the holding position 3, the samples of all the priorities are selected (YES in Step S205). Therefore, the CPU 51a determines that the transport destination is "NO", and returns the process to an invoked address of the sample transport destination determining process.

Next, the CPU 51a determines whether the determined transport destination is the first measurement unit 2 or the second measurement unit 3 (Step S114). Since the determined transport destination is "NO" (NO in Step S114), the CPU refers to the sample processing table PT so as to determine whether or not there is a sample in which the measurement order is not confirmed (Step S106). Here, since the measurement order of the sample at the holding positions 4 to 10 is not confirmed (YES in Step S106), the sample bar-code of the sample at the holding position 4 is read (Steps S107 and S108), and the CPU 51a obtains the measurement order of the sample (Steps S109 and S110). Here, the sample at the holding position 4 is the first sample, and the measurement order includes the CBC+DIFF item but not the second measurement item. Therefore, the information representing "CBC+DIFF" is stored in the field F2 of the measurement order in the row at the holding position 3 in the sample processing table PT, and the information representing "Unmeasured" is stored in the field F3 of the measurement state (Step S111). Furthermore, the CPU 51a determines the priority of the sample requiring processing (Step S112). Here, the samples at the holding positions 3 and 4 correspond to the samples requiring processing. Since none of these samples do include the second measurement item in the measurement order, the priority is assigned to a sequence on the tail side from the head side of the sample rack. That is, the priority of the sample at the holding position 3 becomes "1", and the priority of the sample at the holding position 4 becomes "2". Furthermore, in the sample processing table PT, the information representing "1" is stored in the field F4 of the priority of the sample at the holding position 4.

Figure 18G:
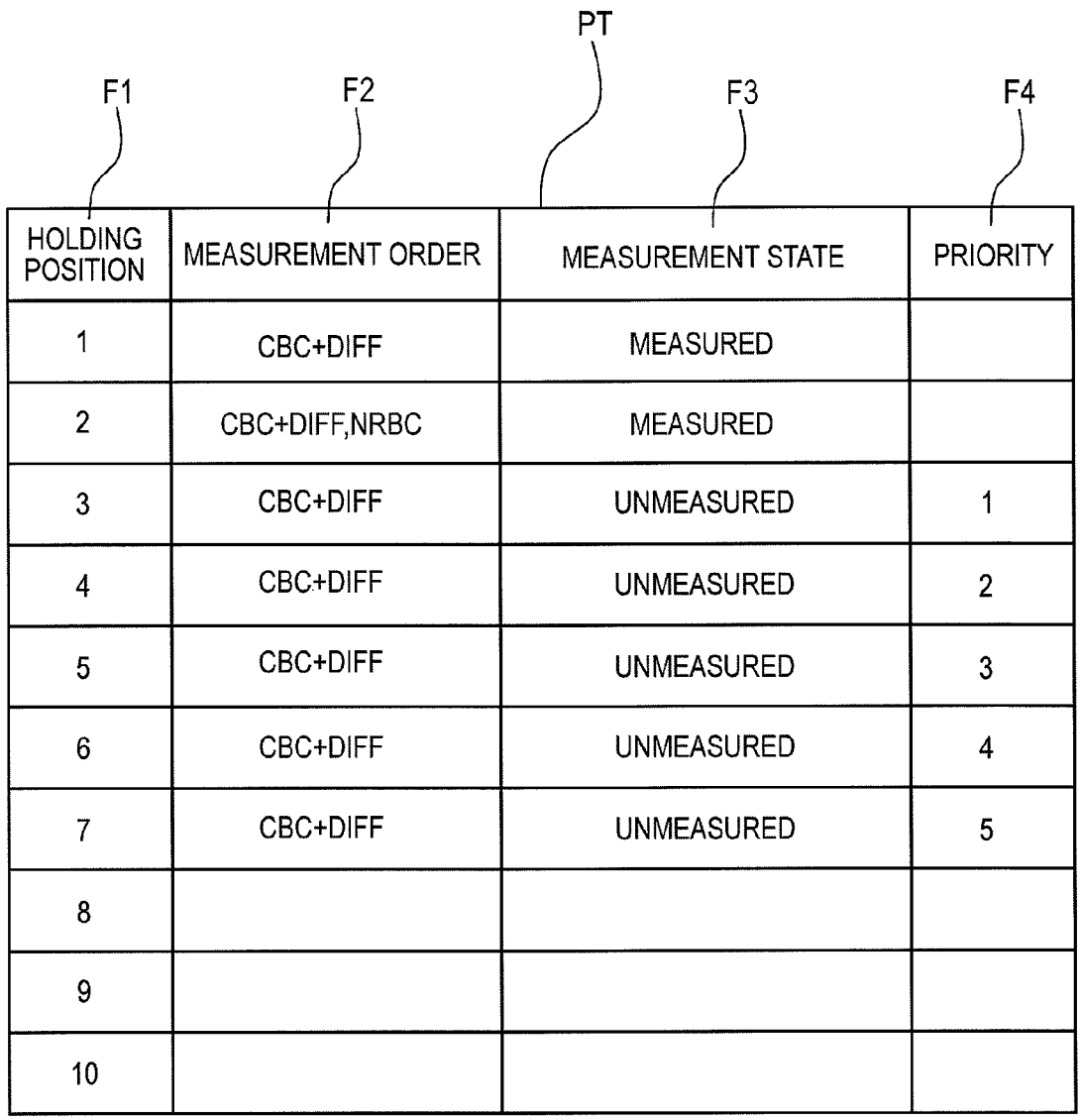
FIG. 18G is a diagram schematically illustrating an example of a state of the sample processing table.

Since all the samples at the holding positions 5 to 7 are the first sample (see FIG. 16), the same process as that of the sample at the above-mentioned holding position 4 is repeatedly performed (Steps S103 to S112). The state of the sample processing table PT updated as described above is shown in FIG. 18G. As shown in FIG. 18G, the priorities 1 to 5 are assigned in the order from the sample at the holding position 3 to the one at the holding position with a smaller number.

The sample at the holding position 8 is the second sample (see FIG. 16). In Steps S103 to S105, the sample at the holding position 8 is also subjected to the same process as that of the samples at the above-mentioned holding positions 4 to 7, and also in the sample transport destination determining process of Step S113, the transport destination is determined as "NO" as in the case of the samples at the holding positions 4 to 7. Furthermore, also in Steps S106 to S111, the same process as that of the samples at the holding positions 4 to 7 are performed.

Since the sample at the holding position 8 is the second sample in the priority determining process of Step S112, the priority is determined as the first priority in accordance with the above-mentioned rule 1. Regarding the holding positions 3 to 7, the priorities 2 to 6 are assigned in order from the one at the holding position with the smallest number.

Figure 18H:
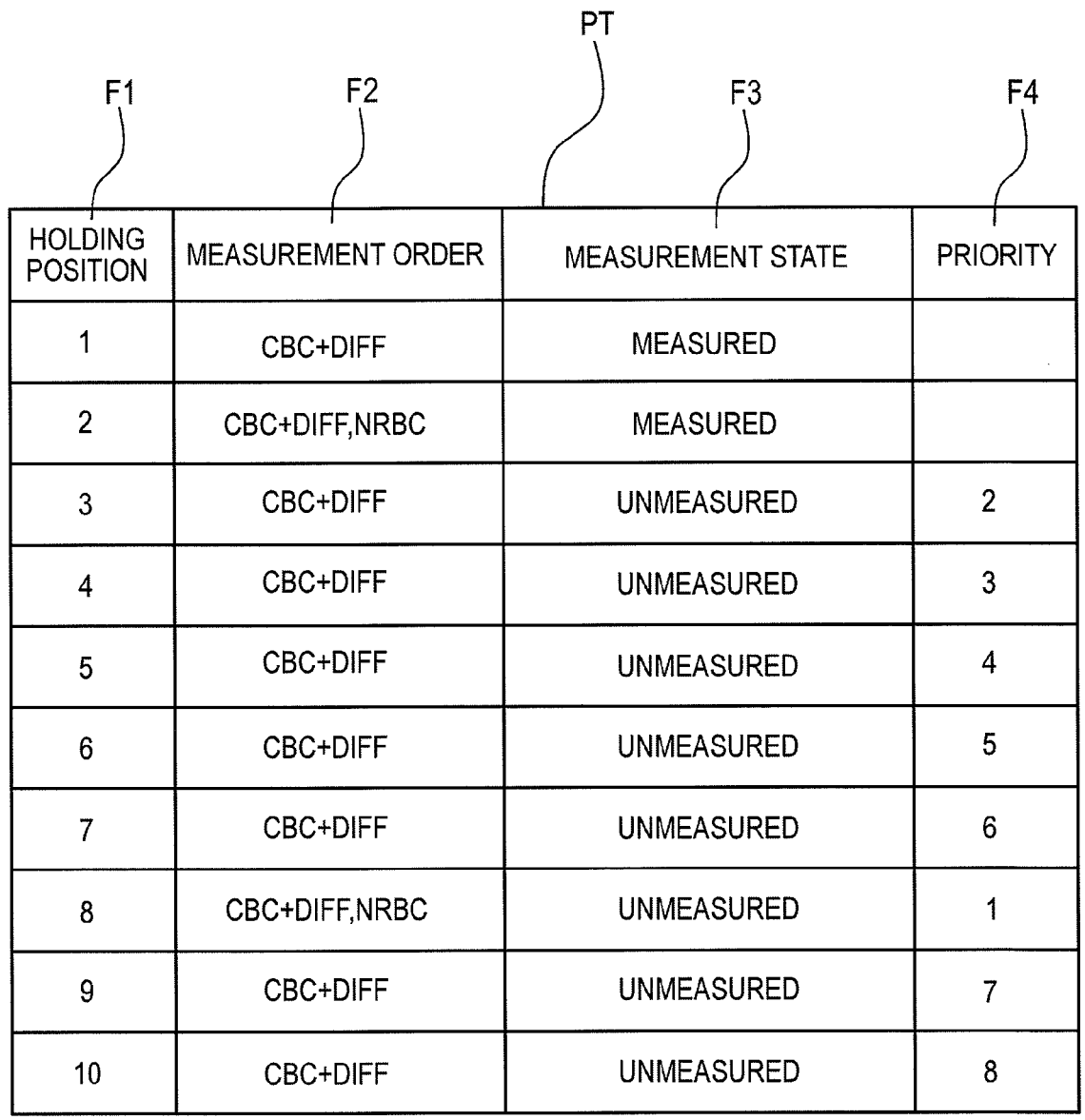
FIG. 18H is a diagram schematically illustrating an example of a state of the sample processing table.

Since all the samples at the holding positions 9 and 10 are the first sample (see FIG. 16), the same process as that of the samples at the above-mentioned holding positions 4 to 7 is repeatedly performed (Steps S103 to S112). In addition, the priority of the sample at the holding position 8 becomes the first priority in accordance with the rule 1, and the samples at the holding positions 3 to 7, 9 and 10 are assigned with the sequences 2 to 8 in the order from the one at the holding position with the smallest number. The state of the sample processing table PT at this point of time is shown in FIG. 18H.

In addition, when sample container loading process relating to the sample container T at the holding position 1 (or 2) is completed in the middle of the processes of reading the sample bar-code, obtaining the measurement order, and determining the priority with respect to the samples at the above-mentioned holding positions 3 to 10, the CPU 51a immediately calculates the sample amount required for measuring with respect to the sample at the holding position 1 (or 2) (Step S305), aspirates the sample from the sample container T (Step S306), and performs the sample container unloading process (Step S307). At this time, the sample rack L is transported such that the holding position 1 (or 2) of the sample rack L is positioned at the first sample supply position 43a (or the second sample supply position 43b) with priority over the reading of the sample bar-code with respect to the samples at the holding positions 3 to 10, and the sample container T is returned to the holding position 1 (or 2) of the sample rack L. For example, when the sample aspirating process S306 relating to the sample container T at the holding position 1 is completed in the middle of reading the sample bar-code of the sample at the holding position 5, the reading of the sample bar-code at the holding position 5 is completed and then the sample rack L is transported such that the holding position 1 of the sample rack L is positioned at the first sample supply position 43a, and the sample container T is returned to the holding position 1. After the sample container T is returned to the sample rack L, the reading of the sample bar-code is restarted so as to read the sample bar-codes relating to the samples at the rest holding positions 6 to 10.

Further, in this example, before the sample loading process is completed on the holding positions 1 and 2, the reading of the sample bar-codes at the holding positions 3 to 10, the obtaining of the measurement orders and the determination of the priority are assumed as being completed.

Thereafter, when the sample container loading process relating to the sample container T at the holding position 1 is completed, the CPU 51a calculates the sample amount required for measuring regarding the sample (Step S305), aspirates the sample from the sample container T (Step S306), and performs the sample container unloading process (Step S307). At this time, the sample rack L is transported such that the holding position 1 of the sample rack L is positioned at the first sample supply position 43a. Therefore, through the above-mentioned sample container unloading process, the sample container T is returned to the holding position 1 of the sample rack L.

In addition, the CPU 51a inputs "Sample Loading Possible" in the state queue Q1 (Step S308). Then, preparing of the measuring reagent (Step S309), detecting of the blood cell (Step S310), cleaning of a flow path, a reaction chamber and the like (Step S311), an analysis process of the measurement data (Step S312), and determining whether or not the retest is necessary and determining of the retest item (Steps S313 to S316) are performed. Further, in this example, it is assumed that the retest of the sample at the holding position 1 is not necessary in Step S313.

When the sample container unloading process carried out by the first measurement unit 2 is completed on the sample at the holding position 1 as described above, the CPU 51a firstly selects the sample at the holding position 8 with the first priority in the sample transport destination determining process S113 (Step S201). Since the second measurement item is included in the measurement order of the sample (YES in Step S202), the CPU determines whether or not the second measurement unit 3 can load a sample in Step S203. At this point of time, the second measurement unit 3 cannot load a sample (NO in Step S203), and the CPU 51a selects the sample at the holding position 3 with the second priority (Steps S205 and S206). Then, since the sample at the holding position 3 is the first sample (NO in Step S202), the CPU 51a determines whether or not the first measurement unit 2 can load a sample (Step S208). Since the first measurement unit 2 is in the state where a sample can be loaded (YES in Step S208), the CPU 51a determines the first measurement unit 2 as the transport destination (Step S209). Then, the sample at the holding position 3 is loaded in the first measurement unit 2, and the sample is measured (see FIG. 17).

Further, while the preparing of the measuring reagent (Step S309), the detecting of the blood cell (Step S310), the cleaning of a flow path, a reaction chamber and the like (Step S311), an analysis process of the measurement data (Step S312), and the determining whether or not the retest is necessary and determining of the retest item (Steps S313 to S316) are performed in the measurement unit, the sample container loading process can be performed in the measurement unit. Therefore, the first measurement unit 2 performs the process of measuring the sample at the holding position 1 in parallel with the process of loading the sample at the holding position 3.

In addition, when the sample container loading process relating to the sample container T at the holding position 2 is completed, the processes of Steps S305, S306 and S307 are carried out similarly to the sample at the holding position 1 as described above, and the sample container T is returned to the holding position 2 of the sample rack L. Then, the processes of the sample measurement and the like of Steps S308 to S316 are performed.

Before the sample container unloading process carried out by the first measurement unit 2 is completed on the sample at the holding position 3, the sample container unloading process carried out by the second measurement unit 3 is completed on the sample at the holding position 2. In the sample transport destination determining process S113, the CPU 51*a* firstly selects the sample at the holding position 8 of which the priority is the first priority (Step S201). Since the second measurement item is included in the measurement order of the sample (YES in Step S202), the CPU determines whether or not the second measurement unit 3 can load a sample in Step S203. Since the second measurement unit 3 is in the state where a sample can be loaded (YES in Step S203), the CPU 51*a* determines the second measurement unit 3 as the transport destination (Step S204). Then, the sample at the holding position 8 is loaded in the second measurement unit 3, and the sample is measured (see FIG. 17).

In the sample processing table PT at this point of time, the measurement state of the samples at the holding positions 1 to 3 and 8 becomes "Measured". For this reason, the priority of the sample at the holding position 4 becomes the first priority. Therefore, when the sample container unloading process carried out by the first measurement unit 2 is completed on the sample at the holding position 3, the transport destination of the sample at the holding position 4 is determined as the first sample measurement unit 2, and the sample loading process carried out by the first measurement unit 2 starts (see FIG. 17).

Next, the sample container unloading process carried out by the second measurement unit 3 is completed on the sample at the holding position 8. In the sample processing table PT at this point of time, the measurement state of the samples at the holding positions 1 to 4 and 8 becomes "Measured". For this reason, the priority of the sample at the holding position 5 becomes the first priority. In addition, the first measurement unit 2 is not in the state where a sample can be loaded, and the second measurement unit 3 is in the state where a sample can be loaded. Therefore, when the sample container unloading process carried out by the second measurement unit 3 is completed on the sample at the holding position 8, the transport destination of the sample at the holding position 5 is determined as the second sample measurement unit 3, and the sample loading process carried out by the second measurement unit 3 starts (see FIG. 17).

Figure 18I:
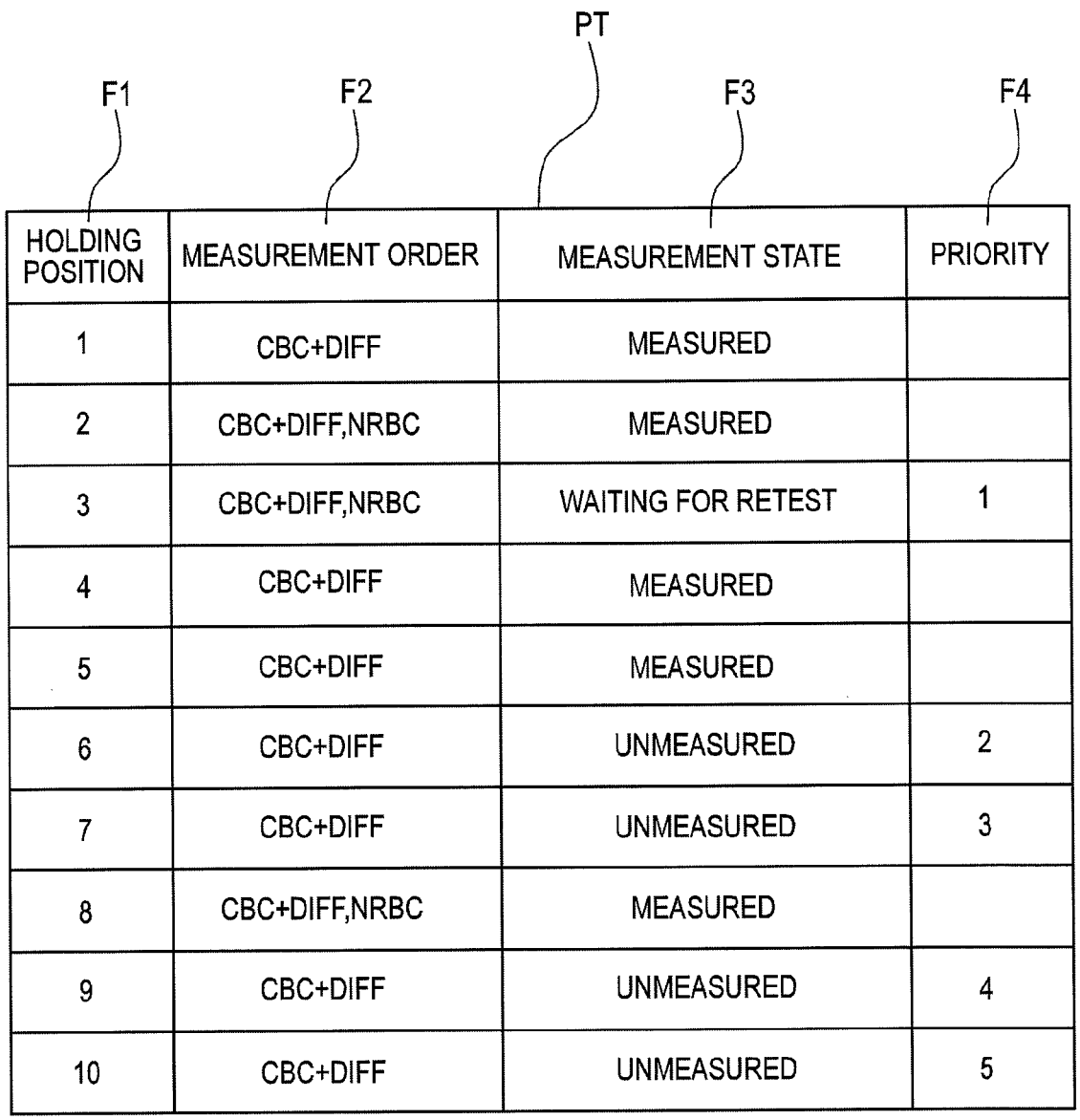
FIG. 18I is a diagram schematically illustrating an example of a state of the sample processing table.

Here, when the numerical value of the WBC of the sample at the holding position 3 exceeds the first numerical range and falls within a second numerical range, it is determined that the retest is necessary and the retest items are determined as the CBC+DIFF item and the NRBC in Step S313. In addition, in Step S315, the data of the measurement order of the sample at the holding position 3 in the sample processing table PT is rewritten with the CBC+DIFF and the NRBC, and the data of the measurement state is rewritten with "Waiting For Retest". Furthermore, in Step S316, the priority is determined, the priority of the sample at the holding position 3 in which the second measurement item is included in the measurement order becomes the first priority, and the priorities of the samples at the holding positions 6, 7, 9 and 10 come to be in the order of 2, 3, 4 and 5. The state of the sample processing table PT at this point of time is shown in FIG. 18I.

Then, the sample container unloading process carried out by the first measurement unit 2 is completed on the sample at the holding position 4. At this point of time, the first measurement unit 2 is in the state where a sample can be loaded, but the second measurement unit 3 is not in the state where a sample can be loaded. Therefore, instead of the sample at the holding position 3 with the first priority, the sample at the holding position 6 with the second priority is determined of the transport destination as the first sample measurement unit 2, and the sample loading process carried out by the first measurement unit 2 starts on the sample (see FIG. 17).

Next, the sample container unloading process carried out by the second measurement unit 3 is completed on the sample at the holding position 5. Here, the second measurement unit 3 is in the state where a sample can be loaded. Therefore, the transport destination of the sample at the holding position 3 with the first priority at this point of time is determined as the second sample measurement unit 3, the second-round sample loading process carried out by the second measurement unit 3 starts on the sample, and the retest of the sample at the holding position 3 is carried out (see FIG. 17).

Next, the sample container unloading process carried out by the first measurement unit 2 is completed on the sample at the holding position 6. In the sample processing table PT at this point of time, the measurement states of the samples at the holding positions 1 to 6 and 8 are "Measured", and the measurement states of the samples at the holding positions 7, 9 and 10 which are the first samples are "Unmeasured". For this reason, the priority of the sample at the holding position 7 becomes the first priority. In addition, the first measurement unit 2 is in the state where a sample can be loaded. Therefore, when the sample container unloading process carried out by the first measurement unit 2 is completed on the sample at the holding position 6, the transport destination of the sample at the holding position 7 is determined as the first sample measurement unit 2, and the sample loading process carried out by the first measurement unit 2 starts on the sample (see FIG. 17).

Next, the sample container unloading process carried out by the second measurement unit 3 is completed on the sample at the holding position 4. In the sample processing table PT at this point of time, the measurement states of the samples at the holding positions 1 to 8 become "Measured". For this reason, the priority of the sample at the holding position 9 becomes the first priority. In addition, the first measurement unit 2 is not in the state where a sample can be loaded, and the second measurement unit 3 is in the state where a sample can be loaded. Therefore, when the sample container unloading process carried out by the second measurement unit 3 is completed on the sample at the holding position 4, the transport destination of the sample at the holding position 9 is determined as the second sample measurement unit 3, and the sample loading process carried out by the second measurement unit 3 starts on the sample (see FIG. 17).

Next, the sample container unloading process carried out by the first measurement unit 2 is completed on the sample at the holding position 7. In the sample processing table PT at this point of time, the measurement states of the samples at the holding positions 1 to 9 are "Measured", and the measurement state of the sample at the holding position 10 which is the first sample is "Unmeasured". For this reason, the priority of the sample at the holding position 10 becomes the first priority. In addition, the first measurement unit 2 is in the state where a sample can be loaded. Therefore, when the sample container unloading process carried out by the first measurement unit 2 is completed on the sample at the holding position 7, the transport destination of the sample at the holding position 10 is determined as the first sample measurement unit 2, and the sample loading process carried out by the first measurement unit 2 starts on the sample (see FIG. 17).

When the sample container unloading process is completed on the samples at the holding positions 9 and 10, the measurement states of all the samples in the sample processing table PT become "Measured" (YES in Step S103). Therefore, the CPU 51*a* completes the sample measuring process on the samples at the holding positions 9 and 10, and then controls the sample transport unit 4 so as to transport the sample rack L to the after-analysis rack holding section 42. As described above, the analysis of all the samples accommodated in the sample rack L is completed.

According to the above-mentioned configuration, since the sample analyzer 1 reacts with the second measurement item in which only some samples such as the NRBC or the RET are measured, there is no need for a configuration to measure the second measurement item in both the first measurement unit 2 and the second measurement unit 3. If only one unit (the second measurement unit 3 in this embodiment) is configured to react with the second measurement item, the entire sample analyzer 1 can react with the second measurement item. In addition, as shown in FIG. 17, after the first measurement unit 2 starts the loading of the sample at the holding position 1 and until the measuring of the sample at the holding position 10 is completed, there is no wasted time in which both the first measurement unit 2 and the second measurement unit 3 are not carrying out the loading or measuring of the sample, so that it can be confirmed that the measurement of the sample is efficiently carried out.

Other Embodiments

Further, in the above-mentioned embodiment, the sample analyzer 1 has been configured to be provided with two measurement units, that is, the first measurement unit 2 and the second measurement unit 3, but the present invention is not limited thereto. The sample analyzer 1 may be configured to be provided with the three or more measurement units capable of measuring the first measurement item and some of these units can measure also the second measurement item. For example, the sample analyzer 1 is provided with three measurement units, that is, the first measurement unit, the second measurement unit and the third measurement unit, so that it may be configured such that the first measurement unit corresponds to the CBC+DIFF item, the second measurement unit corresponds to the CBC+DIFF item and the NRBC, and the third measurement unit corresponds to the CBC+DIFF item and the RET.

In the above-mentioned embodiment, the configuration has been described such that among the plural samples accommodated in the sample rack L, the sample at the holding position 1 is loaded by the first measurement unit 2, and then the bar-codes of the rest samples are sequentially read, but the invention is not limited thereto. It may be configured such that after an instruction to operate the sample measurement is received from an operator and the sample rack L placed at the before-analysis rack holding section 41 is detected, the sample bar-codes of all the samples held on the sample rack are integrally read, all the measurement orders of these samples are read by the information processing unit 5, the priorities of all the samples are determined, and the transport of the samples is carried out on the basis of the priorities and the operation states of the first measurement unit 2 and the second measurement unit 3.

In the above-mentioned embodiment, the configuration has been described such that all the processes of the computer program 54a are performed by the single computer 5a, but the invention is not limited thereto. The same processes carried out by the above-mentioned computer program 54a may be implemented by a distributed system in which the processes are dispersed on and performed by the plural apparatuses (computers).

In the above-mentioned embodiment, the configuration has been described such that both the first measurement unit 2 and the second measurement unit 3 can measure the CBC+DIFF item, but the invention is not limited thereto. It may be configured such that both the first measurement unit 2 and the second measurement unit 3 are configured to be measurable only for the CBC item, and the only the second measurement unit 3 is configured to be measurable for the DIFF item.

In the above-mentioned embodiment, the configuration has been described such that the CBC item and the DIFF item are assumed as the first measurement item, and the RET item and the NRBC item are assumed as the second measurement item, but the invention is not limited thereto. If the item is a measurement item which can be commonly measured in the plural measurement units, the measurement items excepting the CBC item and the DIFF item may be assumed as the first measurement item. If the item is a measurement item which can be measured only in some measurement units among the plural measurement units, the measurement items excepting the RET item and the NRBC item may be assumed as the second measurement item. That is, it may be configured such that both the first measurement unit 2 and the second measurement unit 3 is measurable for the CBC item, the DIFF item and the NRBC item, only the second measurement unit 3 is measurable for the CBC item, the DIFF item, the NRBC item and the RET item. In this case, the CBC item, the DIFF item and the NRBC item correspond to the first measurement item which is the measurement item capable of being commonly measured by the plural measurement units, and the RET item corresponds to the second measurement item which is the measurement item capable of being measured only by some measurement units among the plural measurement units.

In the above-mentioned embodiment, the configuration has been described such that the hand section 25a pulls out the sample container T from the sample rack L transported at a predetermined position by the rack transport section 43, the pulled-out sample container T is transported up to the aspirating position inside the first measurement unit 2 via the loading port 24, and the sample is subjected to the loading by the first measurement unit 2 by aspirating the sample in the sample container T transported at the aspirating position with the aspiration tube, but the invention is not limited thereto. The sample in the sample container T transported at a predetermined position by the rack transport section 43 is aspirated into first measurement unit 2 by the aspiration tube on the rack transport section 43, so that the first measurement unit 2 may carry out the loading of the sample.

In the above-mentioned embodiment, the configuration has been described such that the sample is transported by the sample transport unit 4 to two measurement units 2 and 3 provided in the single sample analyzer 1, but the invention is not limited thereto. It may be configured such that two separated measurement apparatuses each provided at the sample transport unit are connected with a transport line, the sample transport unit receives the sample which is transported to each measurement apparatus by the transport line, and the received sample is transported to the measurement unit in the measurement apparatus.

In the above-mentioned embodiment, the information processing unit 5 performs the obtaining process of the measurement order of the sample and the sample transport controlling process of the sample processing unit 4, but the invention is not limited thereto. The obtaining process of the measurement order of the sample and the sample transport controlling process of the sample processing unit 4 may be performed by the controllers different from each other.

In the above-mentioned embodiment, the measurement unit of the transport destination of the above-mentioned first sample (which includes only the first measurement item in the measurement item) is determined according to the operation states of the first measurement unit 2 and the second measurement unit 3. That is, it is confirmed whether or not the first measurement unit 2 is in the state where a sample can be measured, when the first measurement unit 2 is in the state where a sample can be loaded, the transport destination of the first sample is determined as the first measurement unit 2, and when the first measurement unit 2 is in the state where a sample cannot be loaded, it is confirmed whether or not the second measurement unit 3 is in the state where a sample can be loaded, and when the second measurement unit 3 is in the state where a sample can be loaded, the transport destination of the first sample is determined as the second measurement unit 3, but the invention is not limited thereto. For example, it may be configured such that when the plural first samples are held on the sample rack L, the transport destinations of the first samples corresponding to 60% of the plural first samples are determined as the first measurement unit 2 in advance, and the transport destinations of the first samples corresponding to 40% of the rest samples are determined as the second measurement unit 3 in advance, and the transport order of the plural first samples is randomly determined. Also in this configuration, while the product cost is reduced compared with the related art, it is possible to deal with a number of measurement items.

In the above-mentioned embodiment, the CPU 51a determines the priorities of the samples requiring processing which are held on the sample rack L, and controls the sample transport operation carried out by the sample transport processing unit 4 according to the determined priorities, but the invention is not limited thereto. It may be configured to control the sample transport processing unit 4 such that the priorities of the samples requiring processing are not determined but sequentially transported to the measurement unit from the sample requiring processing located at the head side (downstream side in the transporting direction) of the sample rack L. Also in this configuration, while the product cost is reduced compared with the related art, it is possible to deal with a number of measurement items.

In the above-mentioned embodiment, the detecting section 23 of the first measurement unit 2 and the detecting section 33 of the second measurement unit 3 is configured of the same hardware, and the measuring reagent for the first measurement item is mounted on both the first measurement unit 2 and the second measurement unit 3, and the measuring reagent for the second measurement item is mounted on only the second measurement unit 3. Then, the measurement operation of the first measurement unit 2 is controlled by performing a thread (hereinafter, referred to as a "first measurement item thread") corresponding to the measurement of the first measurement item included in the computer program 54a, and the measurement operation of the second measurement unit 3 is controlled by performing the first measurement item thread and a thread (hereinafter, referred to as a "second measurement thread") corresponding to the measurement of the second measurement item. As a result, the first measurement unit 2 and the second measurement unit 3 are configured to be measurable for the first measurement item, and the second measurement unit 3 is configured to be measurable for the second measurement item in addition to the first measurement item. However, the invention is not limited thereto.

For example, the detecting section 23 of the first measurement unit 2 is configured of hardware capable of measuring the first measurement item, and the detecting section 33 of the second measurement unit 3 is configured of hardware capable of measuring the first measurement item and the second measurement item, that is, hardware different from the detecting section 23 of the first measurement unit 2, so that the first measurement unit 2 and the second measurement unit 3 may be configured to be measurable for the first measurement item and the second measurement unit 3 may be configured to be measurable for the second measurement item in addition to the first measurement item. In this case, the measurement operation of the first measurement unit 2 is controlled by performing the first measurement item thread described above, and the measurement operation of the second measurement unit 3 is controlled by performing the first measurement item thread and the second measurement item thread described above.

In addition, both the detecting section 23 of the first measurement unit 2 and the detecting section 33 of the second measurement unit 3 may be configured as hardware which can measure the first measurement item and the second measurement item. Further, the measurement item which can be measured by the first measurement unit 2 and the second measurement unit 3 may be changed according to the reagent which is accommodated in the measurement unit. For example, when a sensor detects that the measuring reagents for measuring the first measurement item and the measuring reagent for measuring the second measurement item are accommodated in both the first measurement unit 2 and the second measurement unit 3, each of the first measurement unit 2 and the second measurement unit 3 may be controlled to carry out the measurement operation by performing the thread for the first measurement item and the thread for the second measurement item. In addition, for example, when a sensor detects that only a reagent for measuring the first measurement item is accommodated in the first measurement unit 2 and a reagent for measuring the second measurement item is not accommodated in, the first measurement unit 2 may be controlled to carry out the measurement operation by performing a thread for measuring the first measurement item without performing a thread for measuring the second measurement item.

What is claimed is:
1. A sample analyzer comprising:
a first measurement unit configured to measure a sample on a first measurement item;
a second measurement unit configured to measure a sample on the first measurement item and a second measurement item;
a controller; and
a transport unit configured to transport a sample rack which holds a plurality of samples in a transport direction from a before-analysis rack holding section to an after-analysis rack holding section,
wherein a first sample is designated the first measurement item and is not designated the second measurement item,
wherein a second sample is designated the first measurement item and second measurement item,
wherein the controller is programmed to control the transport unit to transport separately first samples to the first measurement unit and the second measurement unit, when the sample rack holds a plurality of first samples,
wherein the controller is further programmed to control the transport unit to transport the second sample to the second measurement unit without transporting the first sample to the second measurement unit based on a measurement item of the second sample, when (a) the first measurement unit is not configured to accept either the first sample or the second sample based on a state of a first measurement unit state data area, (b) the second measurement unit is configured to accept either the first sample or the second sample based on a state of a second measurement state data area, and (c) the sample rack holds: the first sample; and the second sample at more upstream side in the transporting direction than the first sample.

2. The sample analyzer according to claim 1, wherein the controller is further programmed to control the transport unit to transport the second sample to the second measurement unit without transporting the first sample to the second measurement unit based on the measurement item of the second sample, when (a) the first measurement unit is configured to accept either the first sample of the second sample based on the state of the first measurement unit state data area, (b) the second measurement unit is configured to accept either the first sample or the second sample based on the state of the second measurement state data area, and (c) the sample rack holds: the first sample; and the second sample at more upstream side in the transporting direction than the first sample.

3. The sample analyzer according to claim 1, wherein the first measurement unit is not configured to measure a sample on the second measurement item.

4. The sample analyzer according to claim 1, wherein the first measurement item includes at least one CBC item and the second measurement item includes at least one NRBC item.

5. The sample analyzer according to claim 1, wherein the sample rack holds the plurality of samples in a line.

6. The sample analyzer according to claim 1, wherein the controller is further programmed to control the transport unit to transport the first sample to the first measurement unit or the second measurement unit after transporting the second sample.

* * * * *